(12) United States Patent
Wen et al.

(10) Patent No.: US 7,803,932 B2
(45) Date of Patent: Sep. 28, 2010

(54) COMPOSITIONS AND METHODS FOR INHIBITING EB-1-MEDIATED MICROTUBULE STABILITY

(75) Inventors: Ying Wen, San Diego, CA (US); Gregg G. Gundersen, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1 day.

(21) Appl. No.: 11/487,244

(22) Filed: Jul. 14, 2006

(65) Prior Publication Data

US 2007/0148663 A1 Jun. 28, 2007

Related U.S. Application Data

(60) Provisional application No. 60/699,581, filed on Jul. 15, 2005.

(51) Int. Cl.
C07H 21/02 (2006.01)
C07H 21/04 (2006.01)

(52) U.S. Cl. .................... 536/24.5; 536/23.1; 536/24.3; 536/24.33

(58) Field of Classification Search .............. 536/24.5; 514/44

See application file for complete search history.

(56) References Cited

U.S. PATENT DOCUMENTS 6,905,827 B2 * 6/2005 Wohlgemuth et al. .......... 435/6

OTHER PUBLICATIONS

Louie et al, Adenomatous polyposis coli and EB1 localize in close proximity of the mother centriole and EB1 is a functional component of centrosomes. J Cell Sci. Mar. 1, 2004 ;117(Pt 7):1117-28. Epub Feb. 17, 2004.*

Scherer et al, Approaches for the sequence-specific knockdown of mRNA. Nat Biotechnol. Dec. 2003;21(12):1457-65. Review.*
Matsukura et al, Establishment of conditional vectors for hairpin siRNA knockdowns. Nucleic Acids Res. Aug. 1, 2003;31(15):e77.*
Lisa J Scherer & John J Rossi. Approaches for the sequence-specific knockdown of mRNA. Nature Biotechnology, 2003 vol. 21:No. 12:1457-1465.*
Adames, N. R. & Cooper, J. A. Microtubule interactions with the cell cortex causing nuclear movements in *Saccharomyces cerevisiae*. J. Cell Biol. 149, 863-874 (2000).
Alberts, A. S. Identification of a carboxyl-terminal diaphanous-related formin homology protein autoregulatory domain. J. Biol. Chem. 276, 2824-2830 (2001).
Askham, J. M., Moncur, P., Markham, A. F. & Morrison, E. E. Regulation and function of the interaction between the APC tumour suppressor protein and EB 1. Oncogene 19, 1950-1958 (2000).
Askham, J. M., Vaughan, K. T., Goodson, H. V. & Morrison, E. E. Evidence that an interaction between EB 1 and p150 (Glued) is required for the formation and maintenance of a radial microtubule array anchored at the centrosome. Mol. Biol. Cell 13, 3627-3645 (2002).
Beach, D. L., Thibodeaux, J., Maddox, P., Yeh, E. & Bloom, K. The role of the proteins Kar9 and Myo2 in orienting the mitotic spindle of budding yeast. Curr. Biol. 10, 1497-1506 (2000).
Berrueta, L. et al. The adenomatous polyposis coli-binding protein EB 1 is associated with cytoplasmic and spindle microtubules. Proc. Natl Acad. Sci. USA 95, 10596-10601 (1998).

(Continued)

*Primary Examiner*—Sean McGarry
*Assistant Examiner*—Terra Cotta Gibbs
(74) *Attorney, Agent, or Firm*—John P. White; Cooper & Dunham LLP

(57) ABSTRACT

This invention provides a recombinant nucleic acid which, when introduced in vivo into a mammalian cell endogenously expressing EB1, inhibits the expression of EB1 therein, thereby reducing the amount of stable microtubules in the cell.

This invention further provides related compositions, nucleic acids, cells and methods.

5 Claims, 15 Drawing Sheets

OTHER PUBLICATIONS

Berrueta, L., Tirnauer, J. S., Schuyler, S. C., Pellman, D. & Bierer, B. E. The APC-associated protein EB 1 associates with components of the dynactin complex and cytoplasmic dynein intermediate chain. Curr. Biol. 9, 425-428 (1999).

Bienz, M. Spindles cotton on to junctions, APC and EB 1. Nature Cell Biol. 3, E67-E68 (2001).

Bloom, K. It's a kar9ochore to capture microtubules. Nature Cell Biol. 2, E96-E98 (2000).

Cook, T. A., Nagasaki, T. & Gundersen, G. G. Rho guanosine triphosphatase mediates the selective stabilization of microtubules induced by lysophosphatidic acid. J. Cell Biol. 141, 175-185 (1998).

Elbashir, S. M., Harborth, J., Weber, K. & Tuschl, T. Analysis of gene function in somatic mammalian cells using small interfering RNAs. Methods 26, 199-213 (2002).

Evangelista, M., Zigmond, S. & Boone, C. Formins: signaling effectors for assembly and polarization of actin filaments. J. Cell Sci. 116, 2903-2911 (2003).

Fukata, M. et al. Rac 1 and Cdc42 capture microtubules through IQGAP1 and CLIP-170. Cell 109, 873-885 (2002).

Gundersen, G. G. & Bulinski, J. C. Microtubule arrays in differentiated cells contain elevated levels of a post-translationally modified form of tubulin. Eur. J. Cell Biol. 42, 288-294 (1986).

Gundersen, G. G. & Bulinski, J. C. Selective stabilization of microtubules oriented toward the direction of cell migration. Proc. Natl Acad. Sci. USA 85, 5946-5950 (1988).

Gundersen, G. G. Evolutionary conservation of microtubule-capture mechanisms. Nature Rev. Mol. Cell Biol. 3, 296-304 (2002).

Gundersen, G. G., Kalnoski, M. H. & Bulinski, J. C. Distinct populations of microtubules: tyrosinated and nontyrosinated a-tubulin are distributed differently in vivo. Cell 38, 779-789 (1984).

Gundersen, G. G., Khawaja, S. & Bulinski, J. C. Generation of a stable, posttranslationally modified microtubule array is an early event in myogenic differentiation. J. Cell. Biol. 109, 2275-2288 (1989).

Gurland, G. & Gundersen, G. G. Stable, detyrosinated microtubules function to localize vimentin intermediate filaments in fibroblasts. J. Cell Biol. 131, 1275-1290 (1995).

Infante, A. S., Stein, M. S., Zhai, Y., Borisy, G. G. & Gundersen, G. G. Detyrosinated (Glu) microtubules are stabilized by an ATP-sensitive plus-end cap. J. Cell Sci. 113, 3907-3919 (2000).

Karakesisoglou, I., Yang, Y. & Fuchs, E. An epidermal plakin that integrates actin and microtubule networks at cellular junctions. J. Cell Biol. 149, 195-208 (2000).

Kodama, A., Karakesisoglou, I., Wong, E., Vaezi, A. & Fuchs, E. ACF7. An essential integrator of microtubule dynamics. Cell 115, 343-354 (2003).

Kohno, H., Tanaka, K., Mino, A., Umikawa, M. & Takai, Y. Bni 1 implicated in cytoskeletal control is a putative target of Rho 1 p small GTP binding protein in S. cerevisiae. EMBO J. 15, 6060-6068 (1996).

Kreitzer, G., Liao, G. & Gundersen, G. G. Detyrosination of tubulin regulates the interaction of intermediate filaments with microtubules in vivo via a kinesin-dependent mechanism. Mol. Biol. Cell 10, 1105-1118 (1999).

Kusch, J., Liakopoulos, D. & Barral, Y. Spindle asymmetry: a compass for the cell. Trends Cell Biol. 13, 562-569 (2003).

Lee, L., Klee, S. K., Evangelista, M., Boone, C. & Pellman, D. Control of mitotic spindle position by the *Saccharomyces cerevisiae* Formin Bni1p. J. Cell Biol. 144, 947-961 (1999).

Leung, C. L., Sun, D., Zheng, M., Knowles, D. R. & Liem, R. K. Microtubule actin cross-linking factor (MACF): a hybrid of dystonin and dystrophin that can interact with the actin and microtubule cytoskeletons. J. Cell Biol. 147, 1275-1286 (1999).

Liao, G. & Gundersen, G. G. Kinesin is a candidate for cross-bridging microtubules and intermediate filaments. Selective binding of kinesin to detyrosinated tubulin and vimentin. J. Biol. Chem. 273, 9797-9803 (1998).

Ligon, L. A., Shelly, S. S., Tokito, M. & Holzbaur, E. L. The microtubule plus-end proteins EB 1 and dynactin have differential effects on microtubule polymerization. Mol. Biol. Cell 14, 1405-1417 (2003).

Lin, S. X., Gundersen, G. G. & Maxfield, F. R. Export from pericentriolar endocytic recycling compartment to cell surface depends on stable, detyrosinated (glu) microtubules and kinesin. Mol. Biol. Cell 13, 96-109 (2002).

Mimori-Kiyosue, Y., Shiina, N. & Tsukita, S. The dynamic behavior of the APC-binding protein EB 1 on the distal ends of microtubules. Curr. Biol. 10, 865-868 (2000).

Munemitsu, S. et al. The APC gene product associates with microtubules in vivo and promotes their assembly in vitro. Cancer Res. 54, 3676-3681 (1994).

Nakamura, M., Zhou, X. Z., Kishi, S. & Lu, K. P. Involvement of the telomeric protein Pin2/TRF1 in the regulation of the mitotic spindle. FEBS Lett. 514, 193-198 (2002).

Palazzo, A. F. et al. Cdc42, dynein, and dynactin regulate MTOC reorientation independent of Rho-regulated microtubule stabilization. Curr. Biol. 11, 1536-1541 (2001).

Palazzo, A. F., Cook, T. A., Alberts, A. S. & Gundersen, G. G. mDia mediates Rho-regulated formation and orientation of stable microtubules. Nature Cell Biol. 3, 723-729 (2001).

Palazzo, A. F., Eng, C. H., Schlaepfer, D. D., Marcantonio, E. E. & Gundersen, G. G. Localized stabilization of microtubules by integrin and FAK facilitated Rho signaling. Science 303, 836-839 (2004).

Rogers, S. L., Rogers, G. C., Sharp, D. J. & Vale, R. D. *Drosophila* EB 1 is important for proper assembly, dynamics, and positioning of the mitotic spindle. J. Cell Biol. 158, 873-884 (2002).

Schuyler, S. C. & Pellman, D. Microtubule "plus-end-tracking proteins": The end is just the beginning. Cell 105, 421-424 (2001).

Schuyler, S. C. & Pellman, D. Search, capture and signal: games microtubules and centrosomes play. J. Cell Sci. 114, 247-255 (2001).

Su, L. K. et al. APC binds to the novel protein EB 1. Cancer Res. 55, 2971-2977 (1995).

Subramanian, A. et al. Shortstop recruits EB 1/APC1 and promotes microtubule assembly at the muscle-tendon junction. Curr. Biol. 13, 1086-1095 (2003).

Sun, D., Leung, C. L. & Liem, R. K. Characterization of the microtubule binding domain of microtubule actin crosslinking factor (MACF): identification of a novel group of microtubule associated proteins. J. Cell Sci. 114, 161-172 (2001).

Tirnauer, J. S., O'Toole, E., Berrueta, L., Bierer, B. E. & Pellman, D. Yeast Bim1p promotes the Gl-specific dynamics of microtubules. J. Cell Biol. 145, 993-1007 (1999).

Wallar, B. J. & Alberts, A. S. The formins: active scaffolds that remodel the cytoskeleton. Trends Cell Biol. 13, 435-446 (2003).

Watanabe, N., Kato, T., Fujita, A., Ishizaki, T. & Narumiya, S. Cooperation between mDia1 and ROCK in Rho-induced actin reorganization. Nature Cell Biol. 1, 136-143 (1999).

Webster, D. R., Gundersen, G. G., Bulinski, J. C. & Borisy, G. G. Differential turnover of tyrosinated and detyrosinated microtubules. Proc. Natl Acad. Sci. USA 84, 9040-9044 (1987).

Westermann, S. & Weber, K. Post-translational modifications regulate microtubule function. Nature Rev. Mol. Cell Biol. 4, 938-947 (2003).

Yasuda, S. et al. Cdc42 and mDia3 regulate microtubule attachment to kinetochores. Nature 428, 767-771 (2004).

Yin, H., Pruyne, D., Huffaker, T. C. & Bretscher, A. Myosin V orientates the mitotic spindle in yeast. Nature 406, 1013-1015 (2000).

Zumbrunn, J., Kinoshita, K., Hyman, A. A. & Nathke, I. S. Binding of the adenomatous polyposis coli protein to microtubules increases microtubule stability and is regulated by GSK3β phosphorylation. Curr. Biol. 11, 44-49 (2001).

* cited by examiner

Figure 9a-8b (a) Human EB1 DNA Sequence:

ATGGCAGTGAACGTATACTCAACGTCAGTGACCAGTGATAACCTAAGTCGACATGACATGCTGGCCTGGAT
CAATGAGTCTCTGCAGTTGAATCTGACAAAGATCGAACAGTTGTGCTCAGGGGCTGCGTATTGTCAGTTTA
TGGACATGCTGTTCCCTGGCTCCATTGCCTTGAAGAAAGTGAAATTCCAAGCTAAGCTAGAACACGAGTAC
ATCCAGAACTTCAAAATACTACAAGCAGGTTTTAAGAGAATGGGTGTTGACAAAATAATTCCTGTGGACAA
ATTAGTAAAAGGAAAGTTTCAGGACAATTTTGAATTCGTTCAGTGGTTCAAGAAGTTTTTCGATGCAAACT
ATGATGGAAAAGACTATGACCCTGTGGCTGCCAGACAAGGTCAAGAAACTGCAGTGGCTCCTTCCCTTGTT
GCTCCAGCTCTGAATAAACCGAAGAAACCTCTCACTTCTAGCAGTGCAGCTCCCCAGAGGCCCATCTCAA
CACAGAGAACCGCTGCGGCTCCTAAGGCTGGCCCTGGTGTGGTGCGAAAGAACCCTGGTGTGGGCAACGG
AGACGACGAGGCAGCTGAGTTGATGCAGCAGGTCAACGTATTGAAACTTACTGTTGAAGACTTGGAGAAA
GAGAGGGATTTCTACTTCGGAAAGCTACGGAACATTGAATTGATTTGCCAGGAGAACGAGGGGGAAAACG
ACCCTGTATTGCAGAGGATTGTAGACATTCTGTATGCCACAGATGAAGGCTTTGTGATACCTGATGAAGG
GGGCCCACAGGAGGAGCAAGAAGAGTATTAA (b) Human EB1 Protein Sequence:

MAVNVYSTSVTSDNLSRHDMLAWINESLQLNLTKIEQLCSGAAYCQFMDMLFPGSIALKKVKFQAKLEHE
YIQNFKILQAGFKRMGVDKIIPVDKLVKGKFQDNFEFVQWFKKFFDANYDGKDYDPVAARQGQETAVAPS
LVAPALNKPKKPLTSSSAAPQRPISTQRTAAAPKAGPGVVRKNPGVGNGDDEAAELMQQVNVLKLTVEDL
EKERDFYFGKLRNIELICQENEGENDPVLQRIVDILYATDEGFVIPDEGGPQEEQEEY

Figure 10

```
   1 cgagcaggcg gcaggcacgg tccgtgcgga gaggcgagcg agcgggaaga cgcagccacc
  61 ttcctcacca gccagcccac agcggtttgt tcccctttctc gggagtgcgc caatgcctgg
 121 gccgacccaa accctgtccc caaatggcga gaacaacaac gacatcatcc aggataataa
 181 cgggaccatc attccttttcc ggaagcacac agtgcgcggg gagcgttcct acagttgggg
 241 aatggcggtc aatgtgtatt ctacctcgat aacccaagag actatgagca gacatgacat
 301 cattgcatgg gttaatgaca tagtatcttt aaactacaca aaagtgaac agctttgttc
 361 aggagcggcc tattgccaat tcatgacat gctcttccct ggctgcatta gtttgaagaa
 421 agtaaaattt caagcaaagc tggaacatga atatattcac aattttaaac ttctgcaagc
 481 atcatttaag cgaatgaacg ttgataaggt aattccagtg gagaagctag tgaaggacg
 541 tttccaggac aacctgatt ttattcaatg gtttaagaaa ttctatgatg ctaactacga
 601 tgggaaggag tatgatcctg tagaggcacg acaaggcaa gatgcaattc ctcctcctga
 661 ccctgtgaa cagatcttca acctgccaaa aaagtctcac catgcaaact ccccacagc
 721 agtgcagct aaatcaagtc cagcagctaa accaggatcc acacccttctc gaccctcatc
 781 agccaaaagg gcttcttcca gtggctcagc atccaaatcc gataaagatt tagaaacgca
 841 ggtcatacag cttaatgaac agtacattc attaaaactt gcccttgaag gcgtggaaaa
 901 ggaaagggat ttctactttg ggaagttgag agagatcgag ctactctgcc aagaacacgg
 961 gcaggaaaat gatgacctcg tgcagagact aatggacatc ctgtatgctt cagaagaaca
1021 cgagggccac acagaagagc cggaagcaga ggagcaagcc cacgaacagc agccccccgca
1081 gcaggaagag tactgaccca ccccggctgc tcttgacact tccattgtgt gtgggaacgt
1141 ttcttctgga gaattggaac atgtgtggcc ccaagctcaa cagaaaccag ttgttcccaa
1201 tctgccgtta ccatcaacgc actgttgcat atgccagcca ctgcgcttgg ttcccattt
1261 ctttgctaag gtgtattagc ggacggccct ctgccacct acccgagaga tcgtagggtc
1321 acattcatcc aacttcacca cttggctgct tgagattggt tctgtctttt tcttcattcc
1381 tttccagaac aactcttcc caccccaaca ccactgccac cacccctctt tttatcctgg
1441 tgtgaaacaa tggtaatttg atatattgta tttatattgg cattttcaa cccagtgtca
1501 ctagatgtca cacacatttg tggtgctttg atgttttgcaa gtctaacctc tgaacataaa
1561 tttggtcaaa taattggaac aaaggaaac agatacttga tatgaaagcc ataatgacgg
```

Figure 10 continued

```
1621 tgacttgtgt cgtgggggaa aacataaggt catttctctcc ctctactcac aatactaaag
1681 ggaaaaaatg gattcaaagc taggatttca gggccagca gtgttcctcc atcagcatgt
1741 tagacaacta cacagtatgt tgttagttt gaaagacatt cactcaagga aaacaccatc
1801 tcaactttgc ccgctcacca tgtcccttgc cccatgtag cccatttcc agttatgct
1861 ctttcttc tcagggtcct ctttggtggg cagccactcc ccgagatgtt gccatcagtt
1921 ttctgcagtc caaagaggggt atggttaggt acgggtcttc ctgcctcatt cctcttcctc
1981 tttgtgtagg tttcagccac aaaactgtca ttcactctag gggacccta ctaaagggta
2041 acttcaggtg tgcagccctg agctccaagg ctctgcacca tgccacacac ttgctgtaag
2101 gctagaagtg aagaccttat taataggagc ataattgcga gggagaatca tggttctgca
2161 gtctggtgta gacactggaa taacagcaca gaaaaatcta tgactcccaa tatcttctag
2221 aataaagaat tttcccctctt taacacaagg gccctccttg tcattgacct tagctaaacc
2281 atggcaattc ataaatagag gaaacattaa tgaattaaaa gcattcctta ttttttaact
2341 aatatttgta cattctctta gtctcttcc aagtcttgc ctcttttttt tcttatttt
2401 tatttttccc tttgacagat ggtatccctt cctgatcat tcatttcacc ttggtttcta
2461 actttaggtt tactttcact tgttattttga cttagcaggt gcaacaaaaa caagaaacaa
2521 atgtgcccac cccactttcc gcttaactga aaagcttaaa ataaattttcc gaattatg
```

Figure 11

MPGPTQTLSPNGENNNDIIQDNNGTIIPFRKHTVRGERSYSWGMAVNVYST
SITQETMSRHDIIAWVNDIVSLNYTKVEQLCSGAAYCQFMDMLFPGCISLK
KVKFQAKLEHEYIHNFKLLQASFKRMNVDKVIPVEKLVKGRFQDNLDFIQW
FKKFYDANYDGKEYDPVEARQGQDAIPPPDPGEQIFNLPKKSHHANSPTAG
AAKSSPAAKPGSTPSRPSSAKRASSSGSASKSDKDLETQVIQLNEQVHSLK
LALEGVEKERDFYFGKLREIELLCQEHGQENDDLVQRLMDILYASEEHEGH
TEEPEAEEQAHEQQPPQQEEY

Figure 12

```
   1 tctctgtgcg ttgaagccgg agaccgcggc ggcctcagcg aggaccctcc gccccgagc
  61 cgccggccgg agccgcagcc tctgccgcag cgccccccgcc acctgtcccc tcccctccg
 121 cctccgccgg agccgcctcg tgcactctgg ggtatggccg tcaatgtgta ctccacatct
 181 gtgaccagtg aaaatctgag tcgccatgat atgcttgcat gggtcaacga ctccctgcac
 241 ctcaactata ccaagataga acagctttgt tcagggcag cctactgcca gttcatggac
 301 atgctcttcc ccggctgtgt gcacttgagg aaagtgaagt tccaggccaa actagagcat
 361 gaatacatcc acaacttcaa ggtgctgcaa gcagctttca agaagatggg tgttgacaaa
 421 atcattcctg tagagaaatt agtgaaagga aaattccaag ataattttga gtttattcag
 481 tggtttaaga cgcaaactat gatgaaaagg attacaaccc tctgctggcg
 541 cggcagggcc aggacgtagc gccacctcct aaccaggtg atcagatctt caacaaatcc
 601 aagaaactca ttggcacagc agttccacag aggacgtccc ccacaggccc aaaaaacatg
 661 cagacctctg gccggctgag caatgtggcc cccccctgca ttctccggaa gaatcctcca
 721 tcagcccgaa atggcggcca tgagactgat gcccaaattc ttgaactcaa ccaacagctg
 781 gtgacttga agctgacagt ggatggctg gagaaggaaa gtgacttcta cttcagcaaa
 841 cttcgtgaca tcgagctcat ctgccaggag catgaaagtg aaaacagccc tgttatctca
 901 ggcatcattg gcatcctcta tgccacagag gaaggattcg cacccccctga ggacgatgag
 961 attgaagagc atcaacaaga agaccaggac gagtactgag gccggccgca gccctggctg
1021 actgcacggc ttcccgtgc ctccactcc gctccactcc cacattatag tcctttccta
1081 acacggtcgg ccggtgctt tgtgtcagtg ctgcagcact ggagccag gcgaggggg
1141 cttggggca tgggccgga aagcaggcag aagccgtcc tgggtggtgc tgcccagtt
1201 ggtggacccc ctgtccacac ccaccctatt tatttccgtt gtctctctgc tgtgtcgccc
1261 aacacttccc aggtgctgc tgccacccgc cccagccagc cacctgctcc tgacagccag
1321 cagctgtgta tttgacaaag tcattggtat attttttactt actgattct ccttgcactt
1381 tacctgttct tttccagagc tgacagcacg ggctccgcg cagtgtgcct ggcttgctt
1441 cccttcccca tggctggggg ctgggtagg actcacccat tctaatttat tttgtctttt
1501 ggcttctcag tagctaaggg gaaggctgat gtcaggagg gagagaggg ctgaggagt
1561 agtgctgtag gcccagggg tcagggaaag ggaggggggc atgtgaggga tggaaatgac
```

Figure 12 continued

```
1621 ctcctggcac caggctcacc cacccaaggc cccctgcccc agcactgaat cccagcgctg
1681 ccctgaggcc cccagccact ccctccagca gcctggttca ccacacaaac tctgcctgga
1741 cccattgtc tgtctgcttc ccacctgccc tccccacccc ctgcccctcg ggcaccagcc
1801 tgcatatgtg ttcacttta tttaaataaa cttgtgtggt aaaagtacat gccatgtgtc
1861 cctcaactga aaaaaaaaa
```

Figure 13

```
MAVNVYSTSVTSENLSRHDMLAWVNDSLHLNYTKIEQLCSGAAYCQFMDML
FPGCVHLRKVKFQAKLEHEYIHNFKVLQAAFKKMGVDKIIPVEKLVKGKFQ
DNFEFIQWFKKFFDANYDGKDYNPLLARQGQDVAPPPNPGDQIFNKSKKLI
GTAVPQRTSPTGPKNMQTSGRLSNVAPPCILRKNPPSARNGGHETDAQILE
LNQQLVDLKLTVDGLEKERDFYFSKLRDIELICQEHESENSPVISGIIGIL
YATEEGFAPPEDDEIEEHQQEDQDEY
```

COMPOSITIONS AND METHODS FOR INHIBITING EB-1-MEDIATED MICROTUBULE STABILITY

This application claims the benefit of U.S. Provisional Application No. 60/699,581, filed Jul. 15, 2005, the contents of which are incorporated herein by reference into the subject application.

The invention disclosed herein was made with government support from Grant No. GM 62939 from the National Institutes of Health. Accordingly, the U.S. Government has certain rights in this invention.

Throughout this application, various publications are referred to by Arabic numerals within parentheses. Full citations for these publications are presented immediately before the claims. Disclosures of these publications in their entireties are hereby incorporated by reference into this application in order to more fully describe the state of the art to which this invention pertains.

BACKGROUND OF THE INVENTION

In most undifferentiated mammalian cells, microtubule arrays are arranged radially and are composed of highly dynamic microtubules. In many migrating cells and differentiated cells, microtubule arrays become polarized by the formation of a subset of unusually stable microtubules (1-3). In migrating wound-edge cells, stabilized microtubules are selectively formed near the leading edge (2, 4-6). These stable microtubules have a long half-life (>1 h) and are capped at their plus ends (7, 8). Stabilized microtubules accumulate post-translationally modified tubulin, such as detyrosinated tubulin, in which the C-terminal tyrosine of a-tubulin is removed by tubulin carboxypeptidase (9). Stable detyrosinated microtubules (termed Glu-MTs after their C-terminal glutamate) can be distinguished from predominantly tyrosinated dynamic microtubules (Tyr-MTs) with antibodies (10). Stable Glu-MTs may function as specialized tracks for vesicle and cytoskeletal trafficking. Kinesin interacts preferentially with Glu-tubulin in vitro (11), and two kinesin-dependent processes—the recycling of endocytosed transferring (12) and the extension of vimentin intermediate filaments (13, 14)—depend on stable Glu-MTs.

Using wounded monolayers of serum-starved NIH-3T3 fibroblasts, a signaling pathway that regulates stable microtubule formation has been identified. LPA in serum induces polarized stable microtubule formation in wound-edge fibroblasts through the small GTPase Rho and its effector, the formin mDia (4, 5). Stable microtubules induced by LPA-Rho-mDia are the result of microtubule capture and plus-end stabilization, or capping (4, 5). Although this pathway is sufficient to induce stable microtubules in serum-starved adherent fibroblasts, integrin signals, through FAK and lipid rafts, are responsible for restricting the formation of stable microtubules to the leading edge (6).

How mDia induces stable microtubules is not well understood. mDia partially colocalizes with stable microtubules and binds to taxol-stabilized microtubules (5), but whether other proteins are involved in this stabilizing activity has not been explored. As microtubule stabilization occurs primarily at the leading edge and results from the capping of microtubule plus ends, it is possible that microtubule plus-end-binding proteins ('tip proteins') (15) may participate by targeting microtubules to cortical sites and/or contributing to plus-end capping. In budding yeast, an analogous process of microtubule capture occurs at bud sites and is regulated by Rho GTPases and the formin Bni1, the yeast orthologue of mDia (16, 17). Genetic and other studies have identified additional proteins in this process, including the microtubule tip proteins Bim1 (also known as Yeb1) and Kar9 (18-21). Kar9 binds to Bim1 and functions by linking microtubules to actin filaments through Myo2 (22, 23). Microtubules are directed by Myo2 and actin cables towards the bud, where they undergo controlled shrinkage while maintaining their attachment to the bud (18-21). In mammalian cells, EB1 is the orthologue of yeast Bim1 (24), but there is no direct orthologue of Kar9. Because EB1 interacts with the tumour suppressor APC24, and Kar9 and APC have a region of limited sequence homology, it has been proposed that APC may be a functional homologue of Kar9 (25).

EB1 and APC both bind to microtubules in vitro (26, 27) and when either is overexpressed in cells, they bundle and stabilize microtubules (26, 28-30). This is consistent with a role for these proteins in microtubule stabilization. However, the stabilization induced by the overexpressed proteins may result from microtubule bundling, which is not normally observed in cultured cells. It is not clear whether these proteins function in the endogenous regulatory pathway where microtubules are stabilized by a plus-end capture mechanism, as in yeast.

SUMMARY OF THE INVENTION

This invention provides an isolated polypeptide comprising all or a portion of the c-terminal domain of EB1, wherein the isolated polypeptide does not consist of residues 150-268, 219-268 or 185-268 of SEQ. ID. NO:2.

This invention further provides a composition comprising (a) an isolated polypeptide comprising all or a portion of the c-terminal domain of EB1, wherein the isolated polypeptide does not consist of residues 150-268, 219-268 or 185-268 of SEQ. ID. NO:2 and (b) a pharmaceutically acceptable carrier.

This invention further provides a first isolated nucleic acid which encodes a polypeptide comprising all or a portion of the c-terminal domain of EB1, wherein the polypeptide does not consist of residues 150-268, 219-268 or 185-268 of SEQ. ID. NO:2.

This invention further provides a second nucleic acid which, when introduced into an EB1-expressing mammalian cell, inhibits the expression of EB1 therein.

This invention further provides a composition comprising (a) a nucleic acid which, when introduced into an EB1-expressing mammalian cell, inhibits the expression of EB1 therein, and (b) a pharmaceutically acceptable carrier.

This invention further provides a third nucleic acid which encodes nucleic acid which, when introduced into an EB1-expressing mammalian cell, inhibits the expression of EB1 therein.

This invention further provides a cell comprising an expression vector encoding a nucleic acid which, when introduced into an EB1-expressing mammalian cell, inhibits the expression of EB1 therein.

This invention further provides a composition comprising (a) a nucleic acid encoding a nucleic acid which, when introduced into an EB1-expressing mammalian cell, inhibits the expression of EB1 therein, and (b) a pharmaceutically acceptable carrier.

This invention further provides a method for identifying an agent that inhibits EB1-mediated activity in a cell comprising (a) contacting the cell with the agent under conditions which would permit the cell to exhibit a normal EB1 phenotype in the absence of the agent, (b) after a suitable period of time, determining the EB1 phenotype of the cell and (c) comparing the EB1 phenotype of the cell determined in step (b) with the EB1 phenotype determined in the absence of the agent, whereby an abnormal EB1 phenotype in the presence of the agent indicates that the agent inhibits EB1-mediated activity in the cell.

This invention further provides a method for identifying an agent that inhibits EB1 expression in a cell comprising (a) contacting the cell with the agent under conditions which would permit the cell to express EB1 in the absence of the agent, (b) after a suitable period of time, determining the level of EB1 expression in the cell and (c) comparing the level of EB1 expression determined in step (b) with the level of EB1 expression determined in the cell in the absence of the agent, whereby a lower amount of expression in the presence of the agent indicates that the agent inhibits EB1 expression in the cell.

This invention further provides a method for inhibiting EB1-mediated microtubule stabilization in a cell comprising introducing into the cell an amount of the second or third nucleic acid effective to inhibit the expression of EB1 in the cell, thereby inhibiting EB1-mediated microtubule stabilization in the cell.

This invention further provides a method for inhibiting EB1-mediated microtubule stabilization in a cell comprising introducing into the cell an amount of the instant polypeptide or first nucleic acid effective to inhibit EB1 activity in the cell, thereby inhibiting EB1-mediated microtubule stabilization in the cell.

This invention further provides a method for inhibiting EB1-mediated migration of a cell comprising introducing into the cell an amount of the second or third nucleic acid effective to inhibit the expression of EB1 in the cell, thereby inhibiting EB1-mediated cell migration.

This invention further provides a method for inhibiting EB1-mediated migration of a cell comprising introducing into the cell an amount of the instant polypeptide or first nucleic acid effective to inhibit EB1 activity in the cell, thereby inhibiting EB1-mediated cell migration.

This invention further provides a method for inhibiting EB1-mediated mitosis in a cell comprising introducing into the cell an amount of the second or third nucleic acid effective to inhibit the expression of EB1 in the cell, thereby inhibiting EB1-mediated cell mitosis.

This invention further provides a method for inhibiting EB1-mediated mitosis in a cell comprising introducing into the cell an amount of the instant polypeptide or first nucleic acid effective to inhibit EB1 activity in the cell, thereby inhibiting EB1-mediated cell mitosis.

This invention further provides a method for treating a subject afflicted with a condition characterized by metastasizing cells comprising administering to the subject a therapeutically effective amount of the second or third nucleic acid, thereby treating the subject.

This invention further provides a method for treating a subject afflicted with a condition characterized by metastasizing cells comprising administering to the subject a therapeutically effective amount of the instant polypeptide or first nucleic acid, thereby treating the subject.

This invention further provides a method for inhibiting scar formation in a subject following the infliction of physical trauma comprising administering to the subject a prophylactically effective amount of the second or third nucleic acid, thereby inhibiting scar formation in the subject.

This invention further provides a method for inhibiting scar formation in a subject following the infliction of physical trauma comprising administering to the subject a prophylactically effective amount of the instant polypeptide or first nucleic acid, thereby inhibiting scar formation in the subject.

This invention further provides a method for reducing inflammation in a subject comprising administering to the subject a therapeutically effective amount of the second or third nucleic acid, thereby reducing inflammation in the subject.

Finally, this invention further provides a method for reducing inflammation in a subject comprising administering to the subject a therapeutically effective amount of the instant polypeptide or first nucleic acid, thereby reducing inflammation in the subject.

Figures 1A, 1B, 1C, 1D, 1E, 1F:
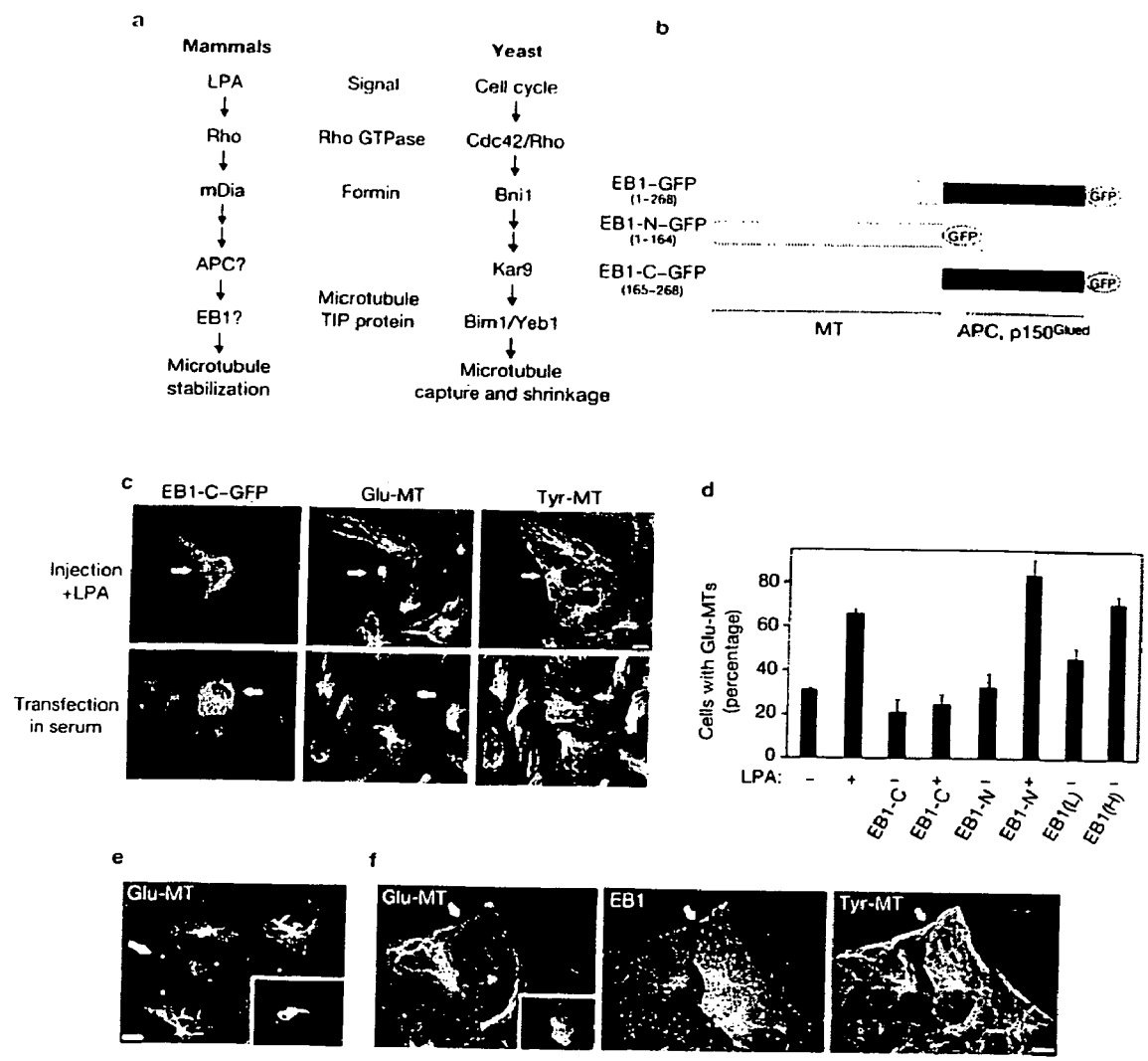
FIG. 1

EB1-C inhibits stable microtubule formation. (a) Comparison of signaling pathways that regulate microtubule stabilization in mammalian cells and microtubule capture and shrinkage in budding yeast. Additional proteins, for example Myo2 and kinesin, are involved in the yeast pathway (see Discussion). (b) Diagram of EB1-GFP constructs. (c) EB1-C is a dominant-negative inhibitor of Glu-MT formation. Expression of microinjected EB1-C-GFP DNA (arrow) inhibits LPA-induced Glu-MT formation in serum-starved wound-edge 3T3 cells (top). Expression of transfected EB1-C-GFP (arrow) reduces Glu-MT levels in NRK-f cells grown in serum (bottom). (d) Quantification of Glu-MTs in starved 3T3 cells expressing microinjected GFP-tagged EB1 constructs, with or without LPA stimulation. EB1(L) and EB1(H) refer to low and high levels of EB1 expression (see main text). Error bars represent the standard error from at least three independent experiments. (e) Cells microinjected with GST-EB1-C (arrow), treated with LPA and then nocodazole did not contain nocodazole-resistant microtubules in contrast to. uninjected cells. Inset shows the injection marker (intermediate filament antibody). (f) Expression of microinjected EB1-C-GFP DNA (arrow and inset) blocked Glu-MT formation, but did not displace or reduce the length of endogenous EB1 from microtubule plus ends. Dynamic Tyr-MTs extended to the leading edge and remained focused at the centrosome. Scale bars represent 10 µm in c, e and f.

FIG. 2

EB1 is necessary and sufficient for stable microtubule formation. (a) Western blot analysis of EB1 levels in COS-7 cells transfected with EB1 siRNA or mock transfected. Vinculin was used as a loading control. (b) NIH 3T3 cells transfected with Cy3-labelled EB1 siRNA did not contain detectable EB1 immunofluorescence (comets) as observed in neighbouring non-transfected cells. (c) EB1 and Glu-MT immunofluorescence in 3T3 cells transfected with EB1 siRNA. Overlay shows EB1 (green), Glu-MTs (red) and DAPI (blue). Cells lacking immunostained EB1 did not contain detectable Glu-MTs (arrows). (d) Quantification of Glu-MTs in LPA-stimulated, starved 3T3 cells after mock- or EB1 siRNA treatment. LPA failed to stimulate Glu-MT formation in EB1 knockdown cells as detected by immunofluorescence (as in c). Error bars represent the standard deviation for two independent experiments. (e) Expression of microinjected full-length EB1-GFP induces Glu-MT formation in serum-starved wound-edge 3T3 cells. A low level of EB1-GFP expression with EB1-GFP restricted to microtubule ends (top). A high level of EB1-GFP expression with EB1-GFP localized along microtubules (bottom). (f) Glu-MTs (green) induced by expression of microinjected EB1-GFP did not incorporate microinjected rhodamine-tubulin (red), whereas dynamic Tyr-MTs (blue) did. Arrows show non-growing Glu-MTs. Scale bars represent 10 µm in b, c, and e, and 2 µm in f.

FIG. 3

EB1 functions downstream of Rho and mDia in the microtubule stabilization pathway. (a) Cells co-injected with EB1-GFP DNA and C3 toxin (a Rho inhibitor) generated Glu-MTs. Inset, human immunoglobulin G injection marker for C3 toxin. (b) GST-DAD did not generate Glu-MTs in the EB1-C-GFP-expressing cells (inset). (c) Cells expressing microinjected EB1-GFP (asterisks and inset) formed Glu-MTs but not actin fibres. The MTOC (arrows) did not reorient in the EB1-GFP-expressing cells. The nucleus is outlined in white. (d) Cells expressing EB1-C-GFP (asterisk and inset) and subsequently treated with LPA did not generate Glu-MTs but still formed actin fibres. The arrow shows that the MTOC reoriented in the LPA-treated, EB1-C-GFP-expressing cell. Scale bar represents 10 µm.

FIG. 4

EB1 binding to APC is important for stable microtubule formation. (a) Comparison of C-terminal sequences of EB1 family members from different organisms shows highly conserved residues within the APC and $p150^{Glued}$ binding domain of mammalian EB1 proteins. Amino-acid numbers are based on the mouse EB1 sequence with identical residues shown in bold. Residues of EB1 that were mutated to the indicated residues (below) are shaded in grey. (b) Diagram of GST-APC constructs used in this study. APC has a microtubule-binding site (labeled 'Basic') and a separate EB1-binding site in its C-terminus. (c) Pull-down analysis of wild type (WT) EB1-C-GFP and mutant EB1-C-GFPs by GST-APC-C1 and GST-$p150^{Glued}$ (1-330). Western blots were probed with anti-GFP antibody. (d) The ability of EB1-C-GFP wild type (WT) and mutants to inhibit LPA-stimulated Glu-MTs in serum-starved 3T3 cells. All EB1-C-GFP constructs were expressed at equivalent levels on the basis of GFP fluorescence. Error bars represent the standard error from at least three independent experiments. (e) EB1-GFP and EB1-C-GFP interact with endogenous APC in cells. COS-7 cells were transiently transfected and immunoprecipitated as indicated. Western blots of the immunoprecipitates were probed with EB1 antibody. (f) EB1-C-GFP expression blocks the interaction of endogenous EB1 with APC-C. Endogenous EB1 bound to GST-APC-C (see GFP lane), but this interaction was disrupted by expression of EB1-C-GFP. The western blot was probed with anti-EB1 antibody. (g) Expression of microinjected full-length APC DNA but not GFP-$p150^{Glued}$ induced Glu-MT formation in starved, wounded 3T3 cells. Cells expressing APC (untagged) were detected with antibody to APC. APC expression did not induce MTOC reorientation (arrow). (h) Expression of microinjected full-length EB1-KR-GFP did not stimulate Glu-MT formation, even though it localized to microtubules. Scale bars represent 10 µm in g and h.

FIG. 5 mDia domain analysis. (a) Glu-MT formation in starved 3T3 cells expressing microinjected DNAs for the indicated GFP-tagged constructs of mDia2. (b) His-tagged 509-1189-mDia1 is the minimal active fragment required for Glu-MT formation. (c) Summary of the ability of different mDia2 constructs to promote Glu-MT formation in starved 3T3 cells and to interact with EB1 and APC (see FIG. 6a, b). For Glu-MT formation, '−' indicates a <15% increase over background, '−/+' indicates a 15-30% increase over background and '+' indicates a >30% increase over background. For each construct tested, n >30. ND, not determined; x, site of G(YEKR) mutation. Scale bars represent 10 µm in a and b.

FIG. 6

EB1 and APC interact with mDia. (a) Binding of in vitro transcribed and translated $^{35}$S-labelled ΔGBD-mDia2 to the indicated GST-tagged constructs of EB1 and APC (bottom). Arrows indicate full-length GST-APC-C or GST-APC-basic proteins. Additional bands detected in the GST-APC-C and GST-APC-basic lanes are presumed to be breakdown products. (b) Binding of in vitro transcribed and translated $^{35}$S-labelled mDia2 fragments to GST-EB1, GST and GST-APC-C. Results are summarized in FIG. 5c. (c) Binding of Flag-mDia1 expressed in COS-7 cells to GST-EB1 and GST-APC-C in the presence of DMSO, nocodazole (NZ) and latrunculin A (Lat A). Bound proteins were detected by western blotting with antibodies to Flag-mDia1, tubulin and actin. (d) Direct interaction of purified recombinant His-521-1040-mDia2 protein to recombinant GST-EB1 and GST-APC proteins. Bound His-mDia was detected by western blotting with an anti-His antibody. (e) Endogenous mDia1 and EB1 co-immunoprecipitate with APC. Mouse brain extracts and COS-7 cell lysates were immunoprecipitated with APC antibodies and precipitates analyzed for APC, mDia1 and EB1 by western blotting with the indicated antibodies. IgG, non-immune immunoglobulin G used for control immunoprecipitation. (f) Schematic representation of the interactions between mDia, EB1 and APC. EB1 and APC bind to mDia through different domains than they use to bind to each other. Note that although EB1 and APC bind to the FH1-FH2 region of mDia, the individual binding sites within this domain have not been mapped. The molecules are not drawn to scale.

FIG. 7

EB1, APC and mDia1 are localized at Glu-MT ends in TC-7 cells. (a) Comparison of the immunolocalization of Glu-MT ends imaged in standard epifluorescence (EPI) and total internal reflection fluorescence (TIRF) microscopy. Segments corresponding to the ends of Glu-MTs are brighter in TIRF images compared with EPI images, indicating the close proximity of Glu-MT ends to the bottom of the cell. (b) Immunolocalization of EB1, APC and mDia1 at Glu-MT ends. In the EB1 images, EB1 puncta on Tyr-MTs are larger than those on Glu-MTs. In the APC and mDia1 images, puncta were found on Glu-MT ends and also in cortical regions away from Glu-MTs. (c) Colocalization of EB1 and APC puncta (arrow) on the end of a Glu-MT (arrow). (d) Quantification of EB1, mDia1 and APC colocalization with Glu-MT ends. 'Shift' refers to random colocalization detected by shifting the images before overlaying (see Methods section). Scale bars represent 1 µm in a, b and c.

FIG. 8

Inhibition of Glu-MT formation by EB1-C inhibits cell migration. Starved 3T3 cells injected with GST (a) or GST-EB1-C-KR (c) protein made Glu-MTs in response to calf serum, maintained position at the wound edge and migrated comparably to non-injected cells. In contrast, starved 3T3 cells injected with GST-EB1-C (b) did not form Glu-MTs and fell behind the wound edge. Scale bar represents 10 µm in a-c. (d) Quantification of microinjected cells that fell behind the wound edge. Error bars represent the standard error for three independent experiments; *P<0.01 compared with GST or GST-EB1-C-KR; **P>0.01 compared with GST.

FIG. 9

(a) Human EB1 nucleotide sequence (SEQ. ID. NO:1) (b) Human EB1 amino acid sequence (SEQ. ID. NO:2)

FIG. 10

Human RP1 nucleotide sequence (SEQ. ID. NO:3)

FIG. 11

Human RP1 amino acid sequence (SEQ. ID. NO:4)

FIG. 12
Human EB3 nucleotide sequence (SEQ. ID. NO:5)
FIG. 13
Human EB3 amino acid sequence (SEQ. ID. NO:6)

DETAILED DESCRIPTION OF THE INVENTION

Terms

"Administering" an agent can be effected or performed using any of the various methods and delivery systems known to those skilled in the art. The administering can be performed, for example, intravenously, orally, nasally, via the cerebrospinal fluid, via implant, transmucosally, transdermally, intramuscularly, and subcutaneously. The following delivery systems, which employ a number of routinely used pharmaceutically acceptable carriers, are only representative of the many embodiments envisioned for administering compositions according to the instant methods.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, ta1blets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

"Agent" shall mean any chemical entity, including, without limitation, a glycomer, a protein, an antibody, a lectin, a nucleic acid, a small molecule, and any combination thereof. Examples of possible agents include, but are not limited to, a ribozyme, a DNAzyme and an siRNA molecule.

"Bacterial cell" shall mean any bacterial cell. One example of a bacterial cell is E. coli.

"C-terminal domain of EB1" shall mean a domain beginning at the carboxyl end of the amino acid sequence that is less than the complete amino acid sequence. For example, the c-terminal domain of EB1 may be the domain corresponding to amino acid residues 165-268 of the EB1 amino acid sequence.

"Cancer" includes, without limitation, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor.

"DNAzyme" shall mean a catalytic nucleic acid that is DNA or whose catalytic component is DNA, and which specifically recognizes and cleaves a distinct target nucleic acid sequence, which can be either DNA or RNA. Each DNAzyme has a catalytic component (also referred to as a "catalytic domain") and a target sequence-binding component consisting of two binding domains, one on either side of the catalytic domain.

"EB1" is used herein to mean end-binding protein 1.

"EB1 Family" is used herein to mean end-binding protein 1, RP1 (e.g., the RP1 having the amino acid sequence show in FIG. 11) and end-binding protein 3 ("EB3") (e.g., the EB3 having the amino acid sequence shown in FIG. 13).

"Expression vector" shall mean a nucleic acid encoding a nucleic acid of interest and/or a protein of interest, which nucleic acid, when placed in a cell, permits the expression of the nucleic acid or protein of interest. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG and a termination codon for detachment of the ribosome. Such vectors may be obtained commercially or assembled from the sequences described in methods well-known in the art.

"Isolated nucleic acid", in one embodiment, means nucleic acid free from other nucleic acid. In another embodiment, a nucleic acid encoding a given polypeptide is isolated if it is free from any nucleic acid encoding a different polypeptide. Isolated nucleic acid can be obtained using known methods.

"Isolated polypeptide" (e.g., EB1), in one embodiment, means a polypeptide free from-other polypeptides. Isolated polypeptides include, for example, polypeptides obtained from cells, and polypeptides produced by chemical and/or recombinant synthesis.

"Mammalian cell" shall mean any mammalian cell. Mammalian cells include, without limitation, cells which are normal, abnormal and transformed, and are exemplified by neurons, epithelial cells, muscle cells, blood cells, immune cells, stem cells, osteocytes, endothelial cells and blast cells.

"Nucleic acid" shall mean any nucleic acid molecule, including, without limitation, DNA (e.g., cDNA), RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Physical trauma" is any incident which results in harm to bodily tissue, and includes, for example, a heat-caused burn, an injury caused by a blunt object, a laceration and a chemical burn. Physical trauma can be incurred, for example, during the course of surgery or other medical procedures, and as the result of an accident.

"Polypeptide" and "protein" are used interchangeably herein, and each means a polymer of amino acid residues. The amino acid residues can be naturally occurring or chemical analogues thereof. Polypeptides and proteins can also include modifications such as glycosylation, lipid attachment, sulfation, hydroxylation, and ADP-ribosylation.

"Ribozyme" shall mean a catalytic nucleic acid molecule which is RNA or whose catalytic component is RNA, and which specifically recognizes and cleaves a distinct target nucleic acid sequence, which can be either DNA or RNA. Each ribozyme has a catalytic component (also referred to as a "catalytic domain") and a target sequence-binding component consisting of two binding domains, one on either side of the catalytic domain.

"siRNA" shall mean small interfering ribonucleic acid. Methods of designing and producing siRNA to decrease the expression of a target protein are well known in the art.

"Therapeutically effective amount" and "prophylactically effective amount" mean an amount sufficient to treat a subject afflicted with, or inhibit the onset of, respectively, a disorder or a complication associated with a disorder. The therapeutically or prophylactically effective amount will vary with the subject, the condition, the agent delivered and the route of delivery. A person of ordinary skill in the art can perform routine titration experiments to determine such an amount. Depending upon the agent delivered, the therapeutically or prophylactically effective amount of agent can be delivered continuously, such as by continuous pump, or at periodic intervals (for example, on one or more separate occasions). Desired time intervals of multiple amounts of a particular agent can be determined without undue experimentation by one skilled in the art. In one embodiment, the therapeutically or prophylactically effective amount is from about 1 mg of agent/subject to about 1 g of agent/subject per dosing. In another embodiment, the therapeutically or prophylactically effective amount is from about 10 mg of agent/subject to 500 mg of agent/subject. In a further embodiment, the therapeutically or prophylactically effective amount is from about 50 mg of agent/subject to 200 mg of agent/subject. In a further embodiment, the therapeutically or prophylactically effective amount is about 100 mg of agent/subject. In still a further embodiment, the therapeutically or prophylactically effective amount is selected from 50 mg of agent/subject, 100 mg of agent/subject, 150 mg of agent/subject, 200 mg of agent/subject, 250 mg of agent/subject, 300 mg of agent/subject, 400 mg of agent/subject and 500 mg of agent/subject.

"Treating" a disorder shall mean slowing, stopping or reversing the disorder's progression. In the preferred embodiment, treating a disorder means reversing the disorder's progression, ideally to the point of eliminating the disorder itself.

"Subject" shall mean any organism including, without limitation, a mammal such as a mouse, a rat, a dog, a guinea pig, a ferret, a rabbit and a primate. In the preferred embodiment, the subject is a human being.

Embodiments of the Invention

This invention provides an isolated polypeptide comprising all or a portion of the c-terminal domain of EB1, wherein the isolated polypeptide does not consist of residues 150-268, 219-268 or 185-268 of SEQ. ID. NO:2. By "does not consist of residues 150-268, 219-268 or 185-268 of SEQ. ID. NO:2", it is stated that in no embodiment of the claimed isolated polypeptide is the polypeptide any of these three specific fragments. However, the claimed polypeptide can comprise all or part of any of these three fragments. In one embodiment, the polypeptide consists of all or a portion of the c-terminal domain of EB1. In another embodiment, the EB1 is mammalian EB1. In another embodiment, the mammalian EB1 is human EB1. In another embodiment, the fragment of EB1 consists of residues 165-268 of SEQ. ID. NO:2.

This invention further provides a composition comprising (a) the instant polypeptide and (b) a pharmaceutically acceptable carrier.

This invention further provides a first isolated nucleic acid which encodes a polypeptide comprising all or a portion of the c-terminal domain of EB1, wherein the polypeptide does not consist of residues 150-268, 219-268 or 185-268 of SEQ. ID. NO:2. In one embodiment, the polypeptide consists of all or a portion of the c-terminal domain of EB1. In another embodiment, the EB1 is mammalian EB1. In another embodiment, the mammalian EB1 is human EB1. In another embodiment, the fragment of EB1 consists of residues 165-268 of SEQ. ID. NO:2. In one embodiment, the nucleic acid is DNA. In another embodiment, the DNA is cDNA. In another embodiment, the nucleic acid is RNA.

This invention also provides a second nucleic acid which, when introduced into an EB1-expressing mammalian cell, inhibits the expression of EB1 therein. In one embodiment, the nucleic acid is siRNA. In another embodiment, the siRNA is a single-stranded, hairpin siRNA. In another embodiment, the siRNA is a double-stranded siRNA. In one embodiment, the nucleic acid is a DNAzyme. In another embodiment, the nucleic acid is a ribozyme. In another embodiment, the nucleic acid is an anti-sense molecule.

This invention also provides a composition comprising (a) a nucleic acid which, when introduced into an EB1-expressing mammalian cell, inhibits the expression of EB1 therein, and (b) a pharmaceutically acceptable carrier.

This invention also provides a third nucleic acid which encodes the nucleic acid which, when introduced into an EB1-expressing mammalian cell, inhibits the expression of EB1 therein. In one embodiment, the nucleic acid is an expression vector.

This invention also provides a cell comprising an expression vector encoding a nucleic acid which, when introduced into an EB1-expressing mammalian cell, inhibits the expression of EB1 therein. In one embodiment, the cell is a bacterial, amphibian, yeast, fungal, insect, or mammalian cell.

This invention also provides composition comprising (a) a nucleic acid encoding a nucleic acid which, when introduced into an EB1-expressing mammalian cell, inhibits the expression of EB1 therein, and (b) a pharmaceutically acceptable carrier.

This invention also provides a method for identifying an agent that inhibits EB1-mediated activity in a cell comprising (a) contacting the cell with the agent under conditions which would permit the cell to exhibit a normal EB1 phenotype in the absence of the agent, (b) after a suitable period of time, determining the EB1 phenotype of the cell and (c) comparing the EB1 phenotype of the cell determined in step (b) with the EB1 phenotype determined in the absence of the agent, whereby an abnormal EB1 phenotype in the presence of the agent indicates that the agent inhibits EB1-mediated activity in the cell. "EB1 phenotype" includes, without limitation, a morphological feature (e.g. microtubule structure, stability or arrangement) or a functional feature (e.g. cell motility, cell migration or cell mitosis).

In one embodiment, the agent is a nucleic acid. In another embodiment, the agent is a polypeptide. In another embodiment, the EB1 is human EB1. In another embodiment, the EB1 is encoded by the nucleic acid sequence set forth in SEQ. ID. NO:1.

This invention also provides a method for identifying an agent that inhibits EB1 expression in a cell comprising (a) contacting the cell with the agent under conditions which would permit the cell to express EB1 in the absence of the agent, (b) after a suitable period of time (i.e., enough time for protein expression to take place), determining the level of EB1 expression in the cell and (c) comparing the level of EB1 expression determined in step (b) with the level of EB1 expression determined in the cell in the absence of the agent, whereby a lower amount of expression in the presence of the agent indicates that the agent inhibits EB1 expression in the cell. In one embodiment, the agent is a nucleic acid. In another embodiment, the agent is a polypeptide. In one embodiment, the EB1 is human EB1. In another embodiment, the EB1 is encoded by the nucleic acid sequence set forth in SEQ. ID. NO:1.

This invention also provides a method for inhibiting EB1-mediated microtubule stabilization in a cell comprising introducing into the cell an amount of the second or third nucleic acid effective to inhibit the expression of EB1 in the cell, thereby inhibiting EB1-mediated microtubule stabilization in the cell.

This invention also provides a method for inhibiting EB1-mediated microtubule stabilization in a cell comprising introducing into the cell an amount of the instant polypeptide or the first nucleic acid effective to inhibit EB1 activity in the cell, thereby inhibiting EB1-mediated microtubule stabilization in the cell.

This invention also provides a method for inhibiting EB1-mediated migration of a cell comprising introducing into the cell an amount of the second or third nucleic acid effective to inhibit the expression of EB1 in the cell, thereby inhibiting EB1-mediated cell migration.

This invention also provides a method for inhibiting EB1-mediated migration of a cell comprising introducing into the cell an amount of the instant polypeptide or the first nucleic acid effective to inhibit EB1 activity in the cell, thereby inhibiting EB1-mediated cell migration.

This invention also provides a method for inhibiting EB1-mediated mitosis in a cell comprising introducing into the cell an amount of the second or third nucleic acid effective to inhibit the expression of EB1 in the cell, thereby inhibiting EB1-mediated cell mitosis.

This invention also provides a method for inhibiting EB1-mediated mitosis in a cell comprising introducing into the cell an amount of the instant polypeptide or the first nucleic acid effective to inhibit EB1 activity in the cell, thereby inhibiting EB1-mediated cell mitosis.

This invention also provides a method for treating a subject afflicted with a condition characterized by metastasizing cells comprising administering to the subject a therapeutically effective amount of the second or third nucleic acid, thereby treating the subject. In one embodiment, the subject is human. In another embodiment, the condition is cancer.

This invention also provides a method for treating a subject afflicted with a condition characterized by metastasizing cells comprising administering to the subject a therapeutically effective amount of the instant polypeptide or the first nucleic acid, thereby treating the subject. In one embodiment, the subject is human. In another embodiment, the condition is cancer.

This invention also provides a method for inhibiting scar formation in a subject following the infliction of physical trauma comprising administering to the subject a prophylactically effective amount of the second or third nucleic acid, thereby inhibiting scar formation in the subject. In one embodiment, the subject is human.

This invention also provides a method for inhibiting scar formation in a subject following the infliction of physical trauma comprising administering to the subject a prophylactically effective amount of the instant polypeptide or the first nucleic acid, thereby inhibiting scar formation in the subject. In one embodiment, the subject is human.

This invention also provides a method for reducing inflammation in a subject comprising administering to the subject a therapeutically effective amount of the second or third nucleic acid, thereby reducing inflammation in the subject. In one embodiment, the subject is human.

Finally, this invention also provides a method for reducing inflammation in a subject comprising administering to the subject a therapeutically effective amount of the instant polypeptide or the first nucleic acid, thereby reducing inflammation in the subject. In one embodiment, the subject is human.

This invention also provides an isolated polypeptide consisting essentially of all or a portion of the c-terminal domain of RP1 or EB3. In one embodiment, the polypeptide consists of all or a portion of the c-terminal domain of RP1 or EB3. In another embodiment, the RP1 or EB3 is mammalian RP1 or EB3. In another embodiment, the mammalian RP1 or EB3 is human RP1 or EB3.

This invention further provides a composition comprising (a) the instant polypeptide and (b) a pharmaceutically acceptable carrier.

This invention further provides a fourth isolated nucleic acid which encodes a polypeptide consisting essentially of all or a portion of the c-terminal domain of RP1 or EB3. In one embodiment, the polypeptide consists of all or a portion of the c-terminal domain of RP1 or EB3. In another embodiment, the RP1 or EB3 is mammalian RP1 or EB3. In another embodiment, the mammalian RP1 or EB3 is human RP1 or EB3. In one embodiment, the nucleic acid is DNA. In another embodiment, the DNA is cDNA. In another embodiment, the nucleic acid is RNA.

This invention also provides a fifth nucleic acid which, when introduced into an RP1- or EB3-expressing mammalian cell, inhibits the expression of RP1 or EB3 therein. In one embodiment, the nucleic acid is siRNA. In another embodiment, the siRNA is a single-stranded, hairpin siRNA.

In another embodiment, the siRNA is a double-stranded siRNA. In one embodiment, the nucleic acid is a DNAzyme. In another embodiment, the nucleic acid is a ribozyme. In another embodiment, the nucleic acid is an anti-sense molecule.

This invention also provides a composition comprising (a) a nucleic acid which, when introduced into an RP1- or EB3-expressing mammalian cell, inhibits the expression of RP1 or EB3 therein, and (b) a pharmaceutically acceptable carrier.

This invention also provides a sixth nucleic acid which encodes the nucleic acid which, when introduced into an RP1- or EB3-expressing mammalian cell, inhibits the expression of RP1 or EB3 therein. In one embodiment, the nucleic acid is an expression vector.

This invention also provides a cell comprising an expression vector encoding a nucleic acid which, when introduced into an RP1- or EB3-expressing mammalian cell, inhibits the expression of RP1 or EB3 therein. In one embodiment, the cell is a bacterial, amphibian, yeast, fungal, insect, or mammalian cell.

This invention also provides composition comprising (a) a nucleic acid encoding a nucleic acid which, when introduced into an RP1- or EB3-expressing mammalian cell, inhibits the expression of RP1 or EB3 therein, and (b) a pharmaceutically acceptable carrier.

This invention also provides a method for identifying an agent that inhibits RP1- or EB3-mediated activity in a cell comprising (a) contacting the cell with the agent under conditions which would permit the cell to exhibit a normal RP1 or EB3 phenotype in the absence of the agent, (b) after a suitable period of time, determining the RP1 or EB3 phenotype of the cell and (c) comparing the RP1 or EB3 phenotype of the cell determined in step (b) with the RP1 or EB3 phenotype determined in the absence of the agent, whereby an abnormal RP1 or EB3 phenotype in the presence of the agent indicates that the agent inhibits RP1- or EB3-mediated activity in the cell. "RP1 or EB3 phenotype" includes, without limitation, a morphological feature (e.g. microtubule structure, stability or arrangement) or a functional feature (e.g. cell motility, cell migration or cell mitosis).

In one embodiment, the agent is a nucleic acid. In another embodiment, the agent is a polypeptide. In another embodiment, the RP1 or EB3 is human RP1 or EB3.

This invention also provides a method for identifying an agent that inhibits RP1 or EB3 expression in a cell comprising (a) contacting the cell with the agent under conditions which would permit the cell to express RP1 or EB3 in the absence of the agent, (b) after a suitable period of time (i.e., enough time for protein expression to take place), determining the level of RP1 or EB3 expression in the cell and (c) comparing the level of RP1 or EB3 expression determined in step (b) with the level of RP1 or EB3 expression determined in the cell in the absence of the agent, whereby a lower amount of expression in the presence of the agent indicates that the agent inhibits RP1 or EB3 expression in the cell. In one embodiment, the agent is a nucleic acid. In another embodiment, the agent is a polypeptide. In one embodiment, the RP1 or EB3 is human RP1 or EB3.

This invention also provides a method for inhibiting RP1- or EB3-mediated microtubule stabilization in a cell comprising introducing into the cell an amount of the fifth or sixth nucleic acid effective to inhibit the expression of RP1 or EB3 in the cell, thereby inhibiting RP1- or EB3-mediated microtubule stabilization in the cell.

This invention also provides a method for inhibiting RP1- or EB3-mediated microtubule stabilization in a cell comprising introducing into the cell an amount of the instant polypeptide or the fourth nucleic acid effective to inhibit RP1 or EB3 activity in the cell, thereby inhibiting RP1- or EB3-mediated microtubule stabilization in the cell.

This invention also provides a method for inhibiting RP1- or EB3-mediated migration of a cell comprising introducing into the cell an amount of the fifth or sixth nucleic acid effective to inhibit the expression of RP1 or EB3 in the cell, thereby inhibiting RP1- or EB3-mediated cell migration.

This invention also provides a method for inhibiting RP1- or EB3-mediated migration of a cell comprising introducing into the cell an amount of the instant polypeptide or the fourth nucleic acid effective to inhibit RP1 or EB3 activity in the cell, thereby inhibiting RP1- or EB3-mediated cell migration.

This invention also provides a method for inhibiting RP1- or EB3-mediated mitosis in a cell comprising introducing into the cell an amount of the fifth or sixth nucleic acid effective to inhibit the expression of RP1 or EB3 in the cell, thereby inhibiting RP1- or EB3-mediated cell mitosis.

This invention also provides a method for inhibiting RP1- or EB3-mediated mitosis in a cell comprising introducing into the cell an amount of the instant polypeptide or the fourth nucleic acid effective to inhibit RP1 or EB3 activity in the cell, thereby inhibiting RP1- or EB3-mediated cell mitosis.

This invention also provides a method for treating a subject afflicted with a condition characterized by metastasizing cells comprising administering to the subject a therapeutically effective amount of the fifth or sixth nucleic acid, thereby treating the subject. In one embodiment, the subject is human. In another embodiment, the condition is cancer.

This invention also provides a method for treating a subject afflicted with a condition characterized by metastasizing cells comprising administering to the subject a therapeutically effective amount of the instant polypeptide or the fourth nucleic acid, thereby treating the subject. In one embodiment, the subject is human. In another embodiment, the condition is cancer.

This invention also provides a method for inhibiting scar formation in a subject following the infliction of physical trauma comprising administering to the subject a prophylactically effective amount of the fifth or sixth nucleic acid, thereby inhibiting scar formation in the subject. In one embodiment, the subject is human.

This invention also provides a method for inhibiting scar formation in a subject following the infliction of physical trauma comprising administering to the subject a prophylactically effective amount of the instant polypeptide or the fourth nucleic acid, thereby inhibiting scar formation in the subject. In one embodiment, the subject is human.

This invention also provides a method for reducing inflammation in a subject comprising administering to the subject a therapeutically effective amount of the fifth or sixth nucleic acid, thereby reducing inflammation in the subject. In one embodiment, the subject is human.

Finally, this invention also provides a method for reducing inflammation in a subject comprising administering to the subject a therapeutically effective amount of the instant polypeptide or the fourth nucleic acid, thereby reducing inflammation in the subject. In one embodiment, the subject is human.

For each of the above methods based on inhibiting microtubule stabilization mediated by EB1, RP1 and/or EB3, the use of one or more agents to inhibit two or more of EB1, RP1 and EB3 is envisioned. That is, the use of agents which individually or in combination inhibit (i) EB1 and RP1, (ii) EB1 and EB3, (iii) RP1 and EB3, and/or (iv) EB1, RP1 and EB3 is envisioned.

This invention will be better understood from the Experimental Details which follow. However, one skilled in the art will readily appreciate that the specific methods and results discussed are merely illustrative of the invention as described more fully in the claims which follow thereafter.

Experimental Details

Synopsis

Because of the similarity in the proteins and the microtubule capture events between yeast and mammals (31) (FIG. 1a), whether EB1 and APC function in the Rho/mDia pathway for microtubule stabilization was tested. Results show that mammalian EB1 and APC function downstream of Rho and mDia to selectively stabilize microtubules in fibroblasts. Both EB1 and APC interact with mDia directly, and domain studies indicate that the three proteins may form a complex. EB1, APC and mDia1 are all detected at stable microtubule ends, which suggests that they may function as a capture complex to stabilize microtubule ends. Selective inhibition of stable microtubule formation with a dominant-negative EB1 construct inhibited cell migration into a wound formed in vitro, showing for the first time the importance of stable microtubules for cell migration.

Introduction

Lysophosphatidic acid (LPA) stimulates Rho GTPase and its effector, the formin mDia, to capture and stabilize microtubules in fibroblasts. Whether mammalian EB1 and adenomatous polyposis coli (APC) function downstream of Rho-mDia in microtubule stabilization was investigated. A carboxy-terminal APC-binding fragment of EB1 (EB1-C) functioned as a dominant-negative inhibitor of microtubule stabilization induced by LPA or active mDia. Knockdown of EB1 with small interfering RNAs also prevented microtubule stabilization. Expression of either full-length EB1 or APC, but not an APC-binding mutant of EB1, was sufficient to stabilize microtubules. Binding and localization studies showed that EB1, APC and mDia may form a complex at stable microtubule ends. Furthermore, EB1-C, but not an APC-binding mutant, inhibited fibroblast migration in an in vitro wounding assay. These results show an evolutionarily conserved pathway for microtubule capture, and suggest that mDia functions as a scaffold protein for EB1 and APC to stabilize microtubules and promote cell migration.

Materials and Methods

All chemicals and reagents were of molecular biology grade and were from Sigma (St. Louis, Mo.) unless otherwise noted. Restriction enzymes were from Promega (Madison, Wis.) and Platinum Taq DNA high-fidelity polymerase was from Invitrogen (Carlsbad, Calif.).

Microinjection and Transfection

Cell culture was performed as described (4, 5, 14). Confluent NIH-3T3 cells were serum starved for 24-48 h and wounded, and cells at the wound edge were microinjected as described (4, 5, 14). To induce stable microtubules, starved cells were treated with LPA (1 µM; 90 min). DNA for microinjection was diluted to 30-300 µgml$^{-1}$ in H—KCl (10 mM Hepes at pH 7.4, 140 mM KCl) or distilled water. Injected cells were incubated at 37° C. for 2-4 h before fixing in −20° C. methanol. In experiments to determine the hierarchy of the pathway, EB1-GFP DNA was co-injected with botulinum C3 toxin (1 µgml$^{-1}$; a gift from K. Aktories) and the injection marker human immunoglobulin G (5 mg ml$^{-1}$). Cells expressing EB1-C-GFP were identified by GFP fluorescence and re-injected with GST-DAD-mDia1 protein (5 mg ml$^{-1}$). To assess microtubule growth, EB1-GFP-expressing cells were microinjected with rhodamine-tubulin and treated as described (5). To assess microtubule stability, cells co-injected with GST-EB1-C and a non-extractable marker (0.5 mg ml$^{-1}$ mouse monoclonal antibody (mAb) to intermediate filaments) were stimulated with LPA and treated with 2 µM nocodazole for 30 min and detergent extracted before fixing as described (4). For migration assays, serum-starved cells were injected at the wound edge with 90 µM of purified recombinant GST-tagged proteins. One hour after injection, calf serum was added to stimulate cell migration. Cells were fixed after migrating for 8-12 h, and the number of injected cells that had fallen behind the wound edge determined. Cells were transfected with Lipofectin or Lipofectamine Plus (Invitrogen). COS-7 cells were transfected with Lipofectamine 2000 (Invitrogen). All transfections were performed according to the manufacturer's protocol.

Immunofluorescence Microscopy

For detection of stable Glu-MTs, cells were stained with rabbit polyclonal antibody SG (ref. 10; 1:400), and for dynamic Tyr-MTs, a rat mAb YL1/2 (1:10; European Collection of Animal Cell Cultures, Salisbury, UK) was used. Depending on the experiment, cells were also stained with the following antibodies: mouse monoclonal antibody to β-tubulin (3F3; 1:200) or actin (C4D6; 1:200; a gift from J. Lessard); mouse monoclonal antibodies to EB1 (1:50) and mDia1 (1:50) (BD Transduction Laboratory, San Jose, Calif.); RGS-His antibody (Qiagen, Valencia, Calif.); APC mouse monoclonal antibodies Ab-1 and Ab-7 (1:50; Oncogene Research Products, San Diego, Calif.); and anti-APC rabbit polyclonal antibody, C-20 (1:50; Santa Cruz Biotechnology, Santa Cruz, Calif.). DAPI (1:1000) and secondary antibodies with minimal cross-species reactivity (Jackson Immuno Research Laboratories, West Grove, Pa.) were used as described (4-6). Epifluorescence microscopy (EPI) was performed as described (5). TIRF microscopy was performed on a Nikon TE2000 equipped with a 60× PlanApo N.A.1.45 objective. Fluorophores were excited by laser illumination using a laser combiner, a single mode fiber optic and an objective-type TIRF illuminator (Nikon, Melville, N.Y.). For excitation of Alexa488 (Molecular Probes, Eugene, Oreg.), Cy3 and Cy5 we used 488 nm, 543 nm and 633 nm laser lines, respectively. Optimized filter cubes were purchased from Chroma Inc (Lititz, Pa.).

Images of cells stained for Glu-MTs and the protein of interest (EB1, mDia or APC) were taken in both EPI and TIRF modes. EPI and TIRF images of Glu-MTs were overlaid and only Glu-MT ends that appeared in both EPI and TIRF images were marked. These marked ends were overlaid onto the dual-colour TIRF images of. Glu-MTs and the protein of interest. Puncta of EB1, APC and mDia were considered to colocalize with Glu-MT ends if they contacted the marked Glu-MT ends. As a control for specific colocalization, the Glu-MT image was shifted arbitrarily by 10 pixels in both X and Y directions, and the shifted image re-overlaid on the EB1, APC or mDia image. As a non-specific staining control, primary antibodies for EB1, APC and mDia were omitted, and the percentage of colocalization subtracted from both shifted and non-shifted data.

EB1 siRNA

3T3 cells were passaged at least three times in DMEM with 10% fetal bovine serum (Gemina, Woodland, Calif.) before plating into 6-well plates the day before transfection. Cells were transfected with 200 nM EB1 siRNA (nucleotides 181-199; 5'-AAGUGAAAUUCCAAGCUAAGC-3' (SEQ ID NO:7) (synthesized by Dharmacon, Lafayette, Colo.)) using 14 µl Transit TKO (Mirus, Madison, Wis.) as described (50). This EB1 sequence is conserved in mice and humans. COS-7 cells were transfected with 200 nM EB1 siRNA using 10 µl Oligofectamine (Invitrogen) in a 35-mm dish with 900 µl OPTI-MEM (Invitrogen). Media was changed to DMEM with 10% fetal bovine serum 4 hs after transfection. EB1 siRNA was labeled with Cy3 using Label IT siRNA Tracker according to the manufacturer's instructions (Mirus). Cells were analyzed 48 h after transfection. Western blots for EB1 knockdown were stained with mouse anti-EB1 (1:400) and anti-vinculin (1:1000; Sigma) and developed with SuperSignal Chemiluminescence reagent (Pierce).

Plasmid Construction

Mouse EB1-N-GFP (amino acids 1-164) and EB1-C-GFP (amino acids 165-268) were constructed from EB1-GFP (35) by PCR using specific primers and subcloned into PGFP-NKB. EB1-GFP and EB1-C-GFP mutants were generated using the QuickChange kit (Stratagene, La Jolla, Calif.) according to the manufacturer's protocol. N-terminal GST-tagged constructs of EB1, EB1-C, EB1-N and p150$^{Glued}$ (1-330) were generated by subcloning into pGEX-2T (Amersham Biosciences, Piscataway, N.J.). GST-APC-C (amino acids 2167-2843) and GST-APC-C1 (amino acids 2674-2843) were a gift from R. Baer. GST-APC-basic (amino acids 2,167-2,674) was generated by deleting the EB1-binding site from GST-APC-C1. His-509-1109-mDia1 and His-521-1040-mDia2 were constructed from full-length mDia1 (40) and mDia2, respectively, by cloning into pQE-30 (Qiagen). GFP-myc-tagged mDia2 fragments were cloned in pEFmEGFP by standard strategies. ΔGBDΔDADG(YEKR)-mDia2 was generated by substituting Tyr 713, Glu 714, Lys 715 and Arg 717 with Gly, leaving Ile 716 intact. For in vitro transcription/translation studies, mDia2 was sub-cloned into vectors containing T7 promoters. All constructs were verified by DNA sequencing. DNA was purified using Midiprep kits from Promega or Qiagen. GST- and His-tagged proteins were purified by standard protocols and dialysed against H-KCl.

Binding Studies

For binding of wild-type and mutant EB1-C-GFP to APC or p150$^{Glued}$, COS-7 cells were transfected with EB1-C-GFP constructs and lysed in PBS containing 1% Triton X-100 and protease inhibitors. Lysates containing equivalent levels of EB1-C-GFP and mutant proteins were incubated with GST-APC-C1, GST-p150$^{Glued}$ (1-330) or GST-bound to glutathione beads for 2 h at 4° C., washed, and eluted with SDS sample buffer. Bound proteins were analyzed by western blotting with rabbit anti-GFP (1:10,000; BD Transduction Laboratory). To investigate whether EB1-C-GFP blocked endogenous EB1 interaction with APC, lysates from GFP or EB1-C-GFP transfected COS-7 cells were incubated with GST-APC-C or GST on beads. Bound proteins were eluted with SDS sample buffer and analyzed by western blotting for EB1.

mDia2 transcripts labeled with $^{35}$S-methionine (Amersham Biosciences) were generated with Quick-Coupled Transcription/Translation Systems (Promega). Equal molar amounts of GST, GST-EB1 or GST-APC on beads were incubated with labeled transcripts for 2 h at 4° C. in PBS containing 1% Triton X-100 and protease inhibitors. After washing, bound proteins were eluted with SDS sample buffer and analyzed by SDS-PAGE. Gels were incubated for 15-30 min in Amplify (Amersham Biosciences), dried and autoradiographed for 1-24 h. Flag-mDia1 (40) was transfected into COS-7 cells, lysates prepared and treated with 0.5 µM latrunculin A, 10 µM nocodazole or DMSO for 1 h on ice. The treated lysates were incubated with GST-tagged constructs as described above and analyzed by western blotting with mouse anti-Flag-M2 antibody (1:10,000; Sigma), rabbit anti-tubulin10 (W2; 1:50,000) and mouse anti-actin (C4D6; 1:50,000). Direct binding was performed by incubating 0.3 µM of His-521-1040-mDia2 to 0.3 µM GST-EB1 or GST-APC constructs in modified RIPA buffer (PBS, 1% Nonidet-P40, 1% sodium deoxycholate, 0.1% SDS and protease inhibitor cocktail) for 18 h at 18° C. as described (29). Bound proteins were analyzed by western blotting with mouse RGS-His antibody (1:10,000).

Immunoprecipitation

For interaction of EB1-GFP and EB1-C-GFP with endogenous APC, COS-7 cells transfected with EB1-GFP and EB1-C-GFP were lysed and immunoprecipitated with anti-APC (Ab-5, Oncogene Research Products) and immunoprecipitated proteins were analyzed by western blotting for EB1 (1:1,000). Endogenous mDia1, EB1 and APC co-immunoprecipitation were performed from COS-7 cell lysates or mouse brain extracts. COS-7 cell lysates were prepared by extracting cells with lysis buffer (20 mM Tris at pH 7.4, 150 mM NaCl, 1% Triton X-100 and a protease inhibitor cocktail) and clarifying the lysate by centrifugation (10 min; 13,000 g). Mouse brain extracts were prepared by homogenizing freshly dissected mouse brains with a Euroturrax T-20 standard homogenizer (IKA Works, Wilmington, N.C.) in lysis buffer and centrifuging (10 min; 13,000 g). Aliquots of the extracts were flash frozen and stored at −80° C. until required. Endogenous APC was immunoprecipitated with either Ab-5 antibody for EB1 or C-20 antibody for mDia1. Non-immune rabbit or mouse immunoglobulin G antibodies were used as controls.

BIND Identifiers

Seven BIND identifiers (www.BIND.ca) are associated with this manuscript: 151168, 151169, 151170, 151171, 151172, 151173 and 151174.

Results

EB1-C Inhibits Stable Microtubule Formation

EB1 has an amino-terminal microtubule-binding domain and a C-terminal domain that interacts with APC24 and the p150$^{Glued}$ subunit of dynactin (29, 30, 32) (FIG. 1b). Whether one of these domains might function as a dominant-negative inhibitor of microtubule stabilization induced by LPA-Rho-mDia was tested. Microinjection of EB1-C fused to green fluorescent protein (EB1-C-GFP) completely blocked LPA-induced Glu-MT formation in serum-starved fibroblasts (FIG. 1c, d). EB1-C, with or without the GFP tag, also reduced Glu-MT levels when transfected into NRK-f (FIG. 1c), NRK-e, NIH-3T3 and COS-7 cells (data not shown). EB1-C was localized diffusely in the cytoplasm, and did not disrupt the radial array of microtubules (FIG. 1c, f). Microinjection of glutathione S-transferase fused to EB1-C (GST-EB1-C) also prevented the LPA-induced formation of microtubules resistant to nocodazole depolymerization (FIG. 1e), a characteristic of stabilized microtubules (2, 4, 5, 8); in contrast, EB1-N-GFP had no effect on Glu-MTs (FIG. 1d). EB1-N-GFP localized along microtubules as previously reported (29) (data not shown). Although EB1-C blocked stable microtubule formation, it did not induce their turnover as microinjection of EB1-C DNA or protein in LPA-treated fibroblasts did not break down pre-existing Glu-MTs for several hours (data not shown).

Proteins of the EB1 family regulate microtubule polymerization (18, 30, 33, 34) and in mammalian cells EB1 also functions in some way to anchor microtubules to the centrosome (29). Whether inhibition of stable microtubule formation by EB1-C was the result of one of these activities that could indirectly affect stable microtubule formation was tested. In EB1-C-GFP-expressing cells lacking Glu-MTs, endogenous EB1 was not displaced from microtubule plus ends, and the length of EB1 segments (which have the appearance of comets) at microtubule ends was indistinguishable from that in non-expressing cells (FIG. 1f). Two other microtubule tip proteins, CLIP-170 and dynactin, were also not displaced (data not shown). Because the length of EB1 comets reflects the rate of microtubule polymerization (35), it was concluded that EB1-C did not grossly alter microtubule polymerization. In addition, the distance between the ends of microtubules and the cell edge was indistinguishable from that in non-expressing cells (FIG. 1c, f). As described earlier (29), microtubule arrays were less focused at the centrosome in some cells expressing EB1-C (data not shown). However, this was detected in only about half of the cells in which Glu-MTs were inhibited (see FIGS. 1c and f for cells with normal focused microtubule arrays), so it cannot account for the inhibitory effect of EB1-C. These results indicate that EB1-C does not interfere with microtubule polymerization, the ability of microtubules to contact cell edges or the loading of tip proteins onto microtubule ends. Instead, EB1 may contribute to the formation of stable microtubules through APC binding (see below).

EB1 is Necessary for Stable Microtubule Formation

Figures 2A, 2B, 2C, 2D, 2E, 2F:
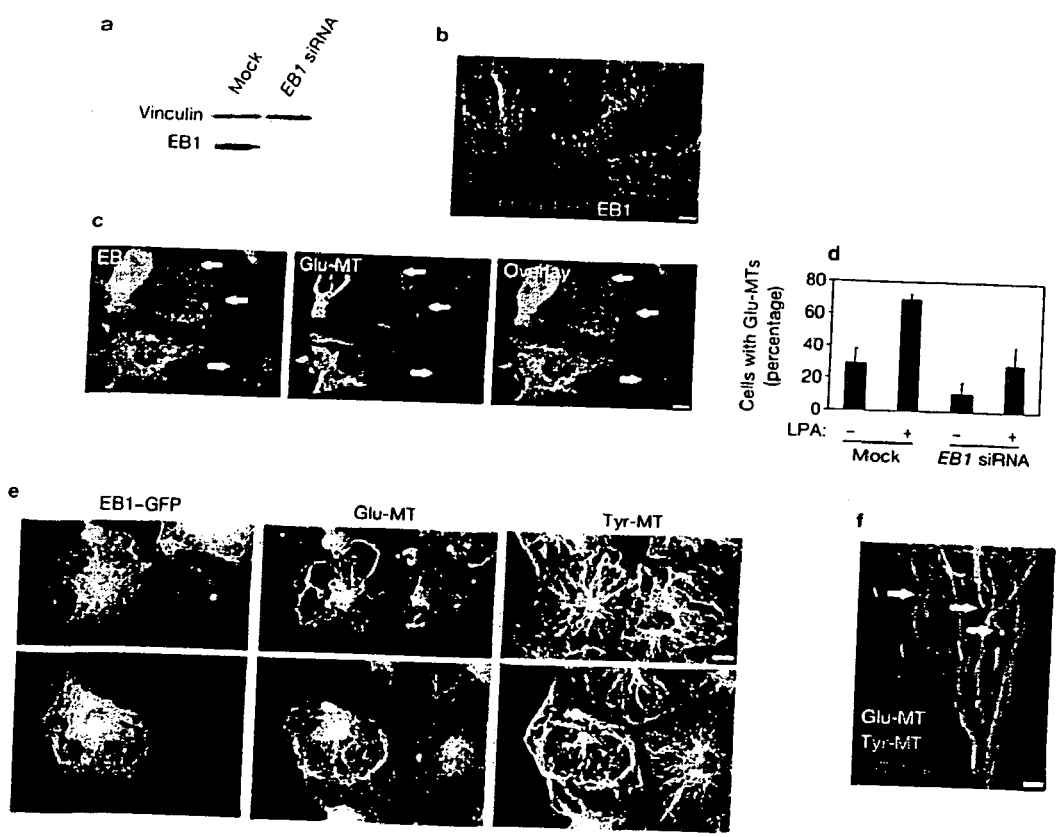

To further investigate the role of EB1 in stable microtubule formation, EB1 expression was knocked down with small interfering RNAs (siRNAs) COS-7 cells transfected with EB1 siRNA had reduced (>80%) EB1 levels (FIG. 2a). In 3T3 fibroblasts containing Cy3-labelled EB1 siRNA, EB1 comets were not detected at microtubule ends (FIG. 2b), highlighting the efficacy of the EB1 siRNA. Glu-MTs were not detected (FIG. 2c), whereas Tyr-MT arrays were normal (data not shown) in EB1-siRNA-transfected cells. LPA induction of Glu-MTs in EB1-siRNA-transfected cells was markedly reduced compared with mock-transfected cells (FIG. 2d). As EB1 knockdown with siRNA and expression of dominant-negative EB1-C both inhibited stable Glu-MT formation in response to LPA, it was concluded that EB1 has an essential role in the formation of stable microtubules.

EB1 Stimulates Stable Microtubule Formation

Next, whether EB1 was sufficient for inducing stable microtubules by expressing EB1-GFP in serum-starved cells without additional stimuli was tested. EB1-GFP induced Glu-MT formation (FIGS. 1d, 2e) similar to the level induced by LPA, active Rho or mDia (4, 5). EB1-GFP induced Glu-MTs at low levels of expression, when its localization was restricted to microtubule plus ends, similar to endogenous EB1 (FIGS. 1d, 2e). At higher levels of expression, EB1 localized along microtubules, more Glu-MTs were formed and more cells contained Glu-MTs (FIGS. 1d, 2e). Similarly to Glu-MTs induced by LPA, those induced by EB1-GFP were polarized towards the wound edge in 65% of the cells. Glu-MTs induced by EB1-GFP were also stable, as judged by an inability to incorporate microinjected rhodamine-tubulin (FIG. 2f) and resistance to nocodazole (data not shown). The induction of stable microtubules by EB1-GFP was not the result of microtubule bundling, as no microtubule bundles were observed even when EB1-GFP decorated the length of microtubules (FIG. 2e).

EB1 Functions Downstream of Rho and mDia

Figures 3A, 3B, 3C, 3D:
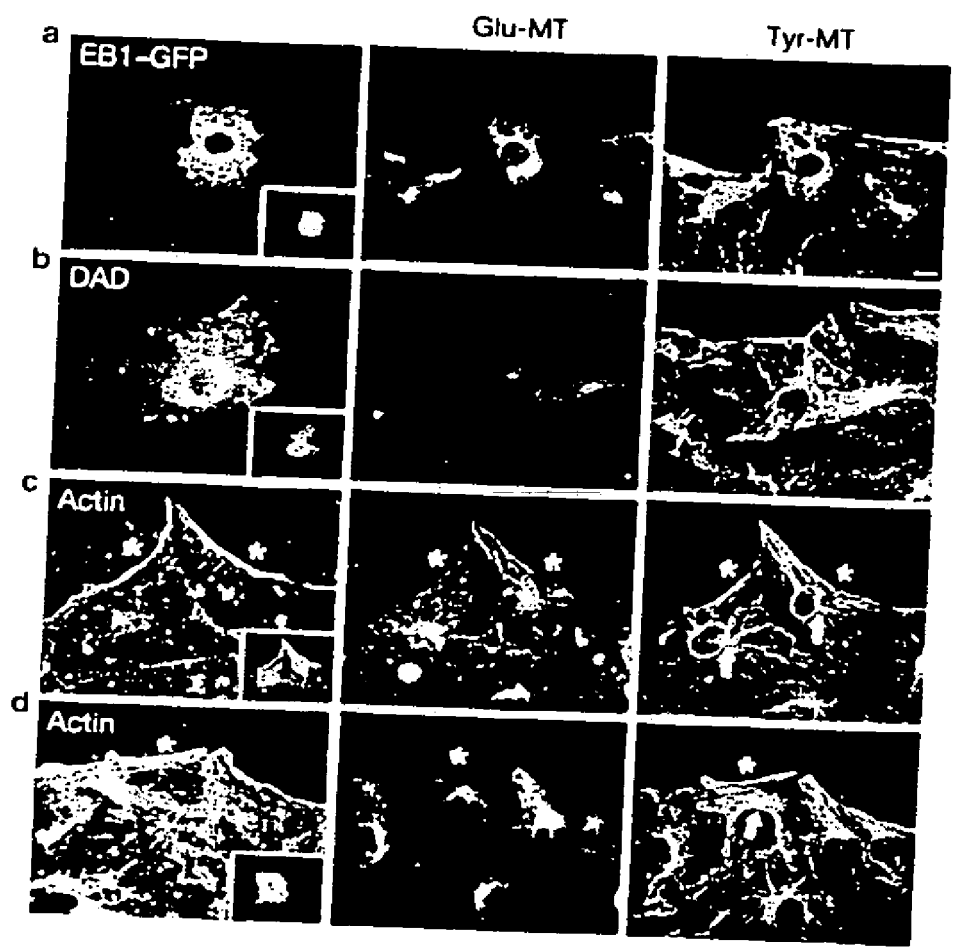

In yeast, Bim1 is downstream of Rho GTPases and Bni1 in the microtubule capture and shrinkage pathway (FIG. 1a). Whether EB1 functions downstream of Rho and mDia to stabilize microtubules in fibroblasts was investigated. When EB1-GFP and the Rho inhibitor C3 toxin were co-injected, EB1-GFP still induced Glu-MT formation (FIG. 3a); conversely, EB1-C-GFP blocked Glu-MT formation induced by the mDia autoregulatory domain (DAD; FIG. 3b), which stimulates endogenous mDia to form both stable microtubules and actin filaments (5, 36). These results show that EB1 functions downstream of Rho and mDia in stabilizing microtubules. However, unlike Rho and mDia, EB1-GFP did not induce actin fibre formation (FIG. 3c) and EB1-C-GFP did not block LPA-induced actin fibre formation (FIG. 3d). Therefore, EB1 functions downstream of LPA-Rho-mDia to regulate microtubules, and this seems to be independent of an effect on actin.

EB1 Does Not Participate in MTOC Reorientation

Previously, it was shown that microtubule stabilization and reorientation of the microtubule-organizing centre (MTOC) in fibroblasts are both triggered by LPA, but are regulated independently by different Rho GTPases and downstream effectors (37). EB1-GFP did not induce MTOC reorientation (FIG. 3c, arrows) and EB1-C-GFP did not inhibit LPA-stimulated MTOC reorientation (FIG. 3d, arrow). These results show that EB1 activity is restricted to the microtubule stabilization pathway and provide further evidence for the independent regulation of the two processes.

Interaction of EB1 and APC in Microtubule Stabilization

Figures 4A, 4B, 4C, 4D, 4E, 4F, 4G, 4H:
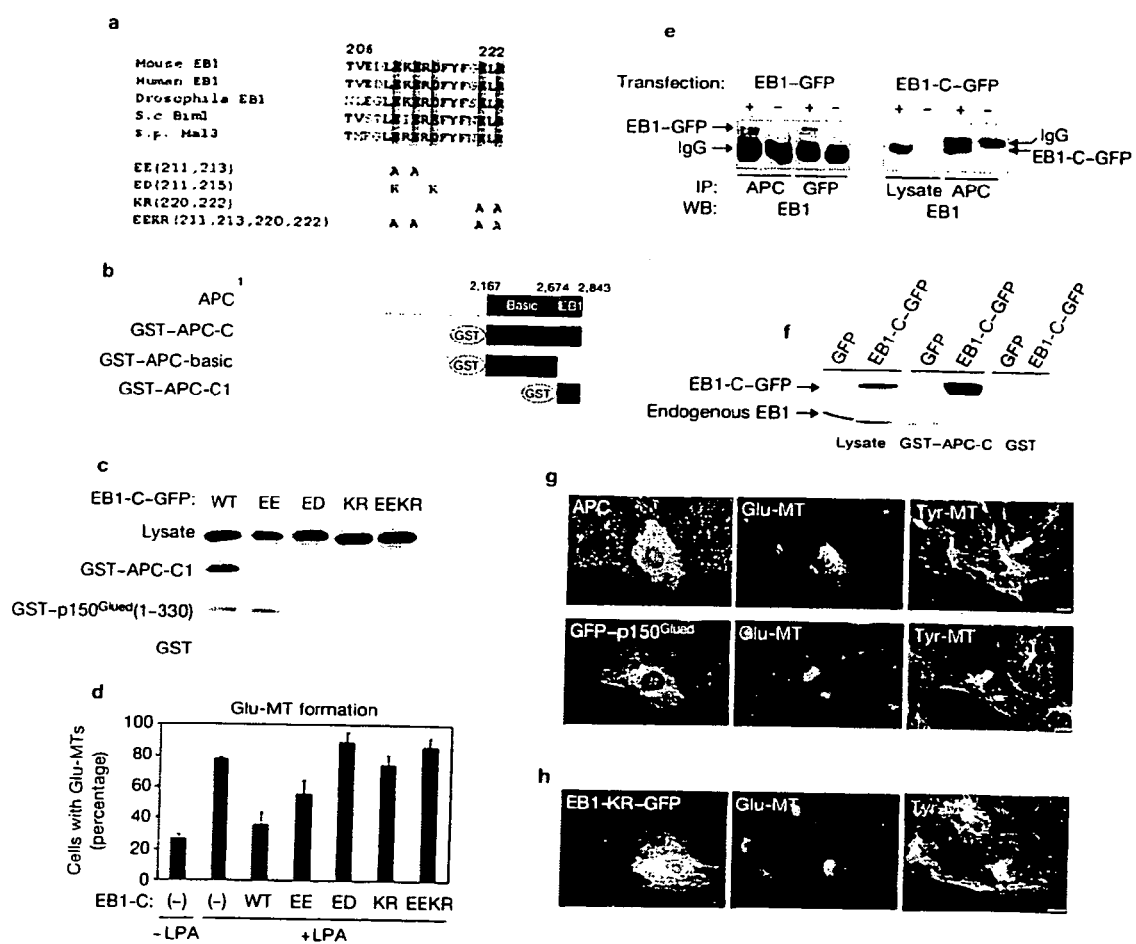

These results suggest that EB1 participates in microtubule stabilization through a novel mechanism. One possibility is that EB1 may enhance the interaction of microtubule ends with proteins that function to capture microtubules. To test this possibility, putative targets for the dominant-negative inhibitory effects of EB1-C were examined. The mammalian EB1 C-terminus contains a conserved domain known to interact with APC24 and p150$^{Glued}$ (29, 30, 32). Amino-acid substitutions were made within this conserved region of EB1-C-GFP (FIG. 4a), and the ability of these mutant proteins to bind to GST-APC-C1 (38) (FIG. 4b) and GST-p150$^{Glued}$ (1-330) fragments (29, 30), which contain the known EB1-binding domain, was tested. At equal loads of expressed EB1-C proteins, wild-type EB1-C-GFP bound to GST-APC-C1 the most strongly, whereas EB1-C-EE-GFP bound much more weakly (FIG. 4c). In contrast, wild-type EB1-C-GFP and EB1-CEE-GFP bound equally to GST-p150$^{Glued}$ (1-330) (FIG. 4c). The other mutants—EB1-C-ED-GFP, EB1-C-KR-GFP and EB1-C-EEKR-GFP—did not bind to either GST-APC-C1 or GST-p150$^{Glued}$ (1-330) (FIG. 4c). These results indicate that the EB1-C mutants can be used to distinguish between binding to APC and p150$^{Glued}$. When the ability of EB1-C mutants to inhibit LPA-induced stable microtubule formation was compared, EB1-C-EE-GFP partially inhibited stable microtubule formation, whereas all the other mutants did not (FIG. 4d). These results suggest that the interaction of EB1 with APC, but not p150$^{Glued}$, is important for stable microtubule formation.

The idea that APC was the target for EB1-C was further tested. Both expressed EB1-GFP and EB1-C-GFP were recovered in APC immunoprecipitates (FIG. 4e). Expression of EB1-C-GFP also prevented endogenous EB1 from interacting with GST-APC-C (FIG. 4f), indicating that the dominant-negative effect of EB1-C is most probably the result of its ability to prevent the EB1-APC interaction.

Expression of full-length APC induced Glu-MT formation, but not MTOC reorientation in cells (FIG. 4g). In contrast, expression of GFP-p150$^{Glued}$ did not induce Glu-MT formation (FIG. 4g). Furthermore, full length EB1 with the KR mutation (EB1-KR-GFP) that prevents interaction with APC (FIG. 4a, c) did not induce Glu-MT formation (FIG. 4h) even though it bound to microtubules. These results show that binding of EB1 to microtubules is not sufficient for inducing stable microtubule formation, but probably requires interaction between EB1 and APC.

EB1 and APC Bind Directly to mDia

Figures 5A, 5B, 5C:
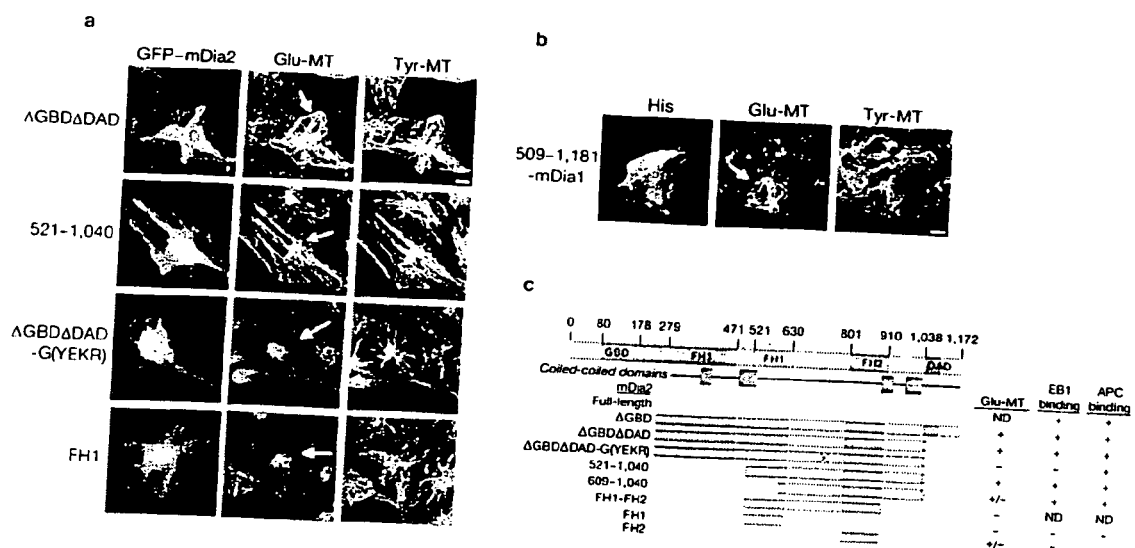

Previously, it was found that constitutively active mDia2 lacking the Rho regulatory domain (ΔGBD-mDia2) and DAD stimulated Glu-MT formation (5). Here, it is reported that smaller fragments also stimulated Glu-MT formation (FIG. 5a, c). The minimally active mDia2 fragment (amino acids 521-1,040) contained the FH1, FH2 and the C-terminal coiled-coiled domains (FIG. 5a, c). The corresponding mDia1 fragment, 509-1,189 (fused to 6× His), was also active (FIG. 5b). These results indicate that the GBD, FH3 and DAD domains are not required for microtubule stabilization. Smaller fragments containing the FH1 domain, the FH2 domain or the FH1-FH2 domains were not fully active (FIG. 5a, c), indicating that multiple domains are necessary for full activity of mDia towards microtubules. Consistent with this idea, a mutation in a conserved region adjacent to the FH2 domain (ΔGBDΔDAD-G(YEKR)-mDia2) blocked the ability of ΔGBDΔDADmDia2 to stimulate Glu-MT formation (FIG. 5a, c).

Figures 6A, 6B, 6C, 6D, 6E, 6F:
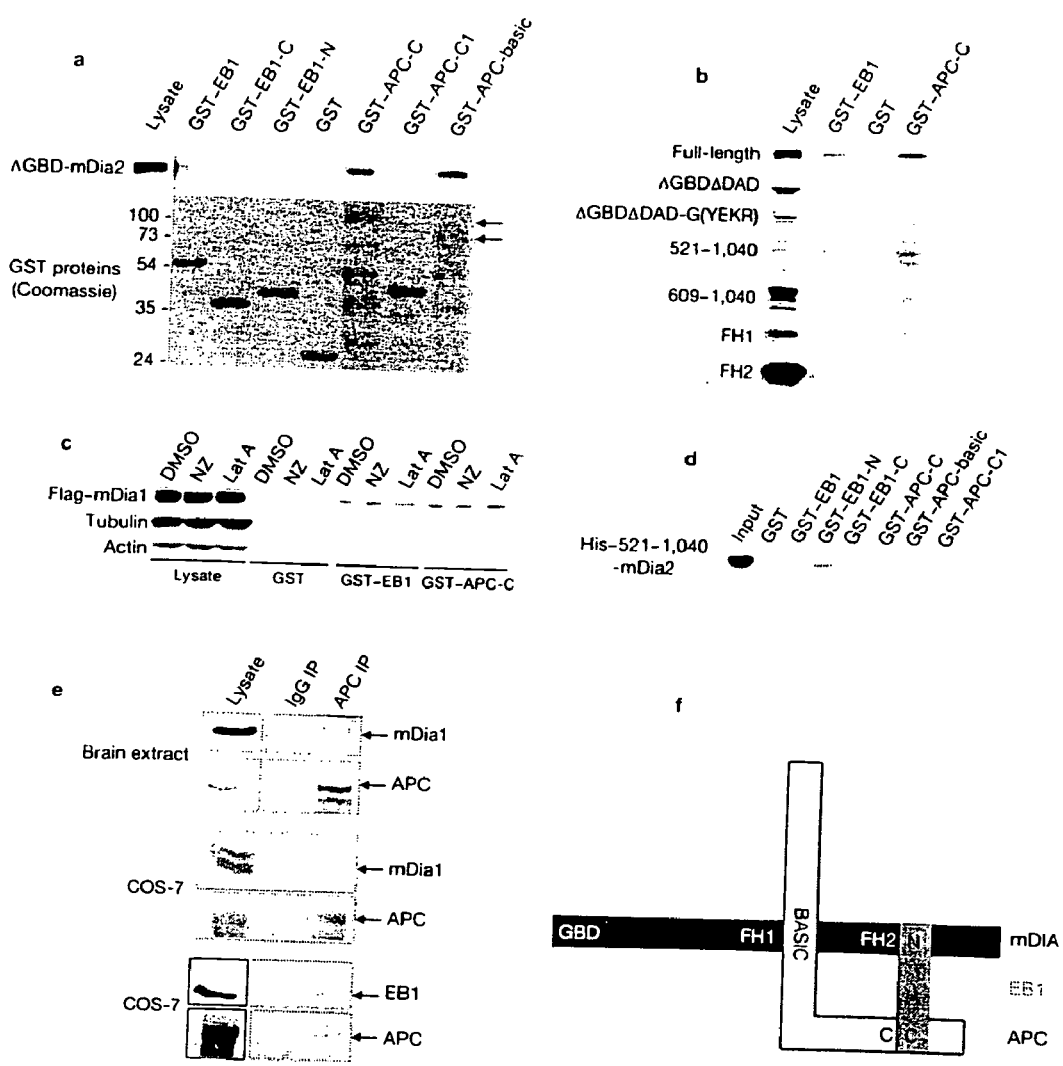

Next, whether mDia interacted with EB1 or APC was tested. Constitutively active ΔGBD-mDia2 made by in vitro transcription/translation bound to both GST-EB1 and GST-APC-C, but not GST (FIG. 6a). The domains of EB1 and APC responsible for binding to ΔGBD-mDia2 were distinct from the domains involved in the interaction between EB1 and APC. Thus, ΔGBD-mDia2 bound to GST-EB1-N, but not to GST-EB1-C, and to GST-APC-basic, but not to GST-APC-C1 (FIG. 6a). The 521-1040-mDia2 fragment also bound to both GST-EB1 and GST-APC-C (FIGS. 5c and 6b). Although 609-1,040-mDia2 did not fully stimulate stable microtubule formation, it did bind to EB1 and APC. Interestingly, ΔGBDΔDADG(YEKR)-mDia2 bound to APC, but not to EB1 (FIGS. 5c and 6b), suggesting that mDia2 binds to APC independently of EB1. Because this construct did not induce stable microtubules, it implies that the mDia-EB1 interaction is necessary for stable microtubule formation. Individual FH1 or FH2 domains did not bind to either EB1 or APC.

Full-length mDia1 also bound to GST-EB1 and GST-APC-C (FIG. 6c). The binding occurred in the presence of either the microtubule-depolymerizing drug nocodazole or the actin-disrupting drug latrunculin A. Neither tubulin nor actin was present in the pull downs (FIG. 6c), indicating that these interactions occurred independently of either microtubules or microfilaments. Direct binding was demonstrated with purified recombinant proteins. His-tagged 521-1,040-mDia2 interacted with GST-EB1 and GST-EB1-N, but not GST-EB1-C (FIG. 6d). It also interacted with GST-APC-C, GST-APC-basic but not GST-APC-C1 (FIG. 6d). These data demonstrate that EB1 and APC interact with mDia directly and independently, and could form a complex (FIG. 6f).

Consistent with the formation of a complex, endogenous EB1 and mDia1 were detected in immunoprecipitates of APC from COS-7 cells, (FIG. 6e). mDia1 and APC also co-immunoprecipitated from mouse brain extract (FIG. 6e). The small amounts of EB1 and mDia1 coimmunoprecipitating with APC may reflect weak interactions or tight regulation of the interacting species.

EB1, APC and mDia1 Localize to Stable Glu-MT Ends

Figures 7A, 7B, 7C, 7D:
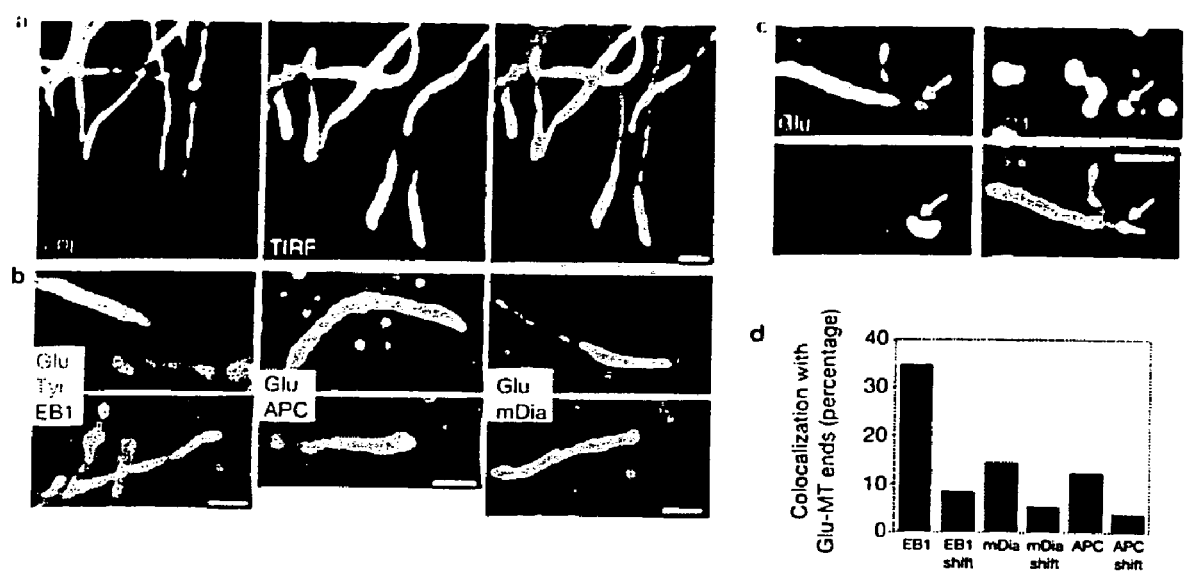

Previous studies using epifluorescence microscopy did not detect EB1 or APC on Glu-MT ends (8). To enhance the detection of these proteins, total internal reflection fluorescence (TIRF) microscopy of TC-7 cells was used, which have readily detectable capped Glu-MT ends (8, 10). A comparison between epifluorescence and TIRF microscopy showed that many Glu-MT ends, but not their shafts, were detected by TIRF (FIG. 7a). This indicates that the ends of Glu-MTs were within the cortical region at the very bottom of the cell, a location consistent with their tethering to cortical factors. This also allowed an examination of these microtubule ends at a high signal-to-noise ratio for EB1, APC and mDia1.

Small EB1 puncta were detected on many Glu-MT ends (FIG. 7b, d). These puncta were much smaller than those on dynamic microtubule ends and did not have a comet-tail appearance (FIG. 7b). Both APC and mDia were also detected as small puncta on Glu-MT ends (FIG. 7b). These puncta seemed to be localized specifically at Glu-MTs ends as shifting the images before overlaying (see Methods section) reduced the extent of colocalization (FIG. 7d).

Whether EB1 colocalized with either APC or mDia1 at Glu-MT ends was also investigated. Because of antibody incompatibilities, it was possible only to colocalize EB1 and APC. In about half of the cases where EB1 puncta were detected at Glu-MTs ends, APC was also detected (FIG. 7c) These results show that all three proteins can be detected at Glu-MT ends, and raise the possibility that they regulate microtubule stability by functioning at microtubule ends.

The Role of Stable Microtubules in Cell Migration

Figures 8A, 8B, 8C, 8D:
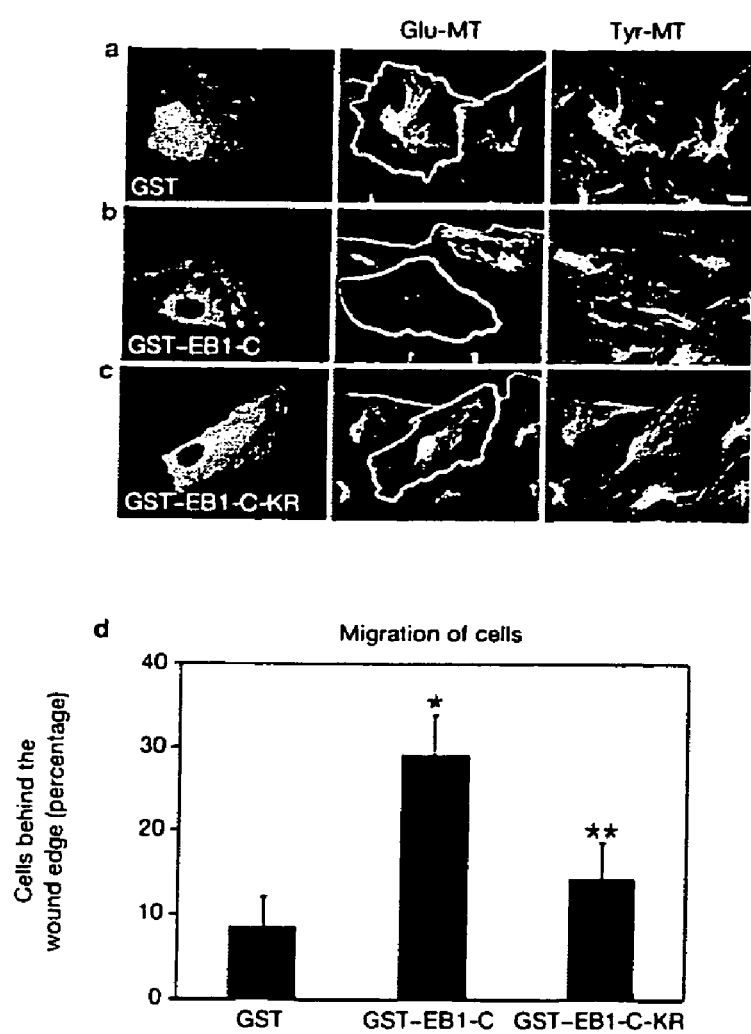

The fact that EB1-C, but not EB1-C-KR, inhibited stable microtubule formation was used to investigate the role of stable Glu-MTs in cell migration. In the migration assay (see Methods section), wound-edge cells injected with GST-EB1-C tended to fall behind the wound edge and had reduced levels of Glu-MTs (FIG. 8d). In contrast, most of the cells injected with either GST or GST-EB1-C-KR had Glu-MTs and migrated equally with uninjected cells (FIG. 8). These results suggest that the formation of stable microtubules is important for cell migration.

Discussion

On the basis of similarities to a yeast pathway regulating microtubule capture at bud sites (31), the role of EB1 and APC in the LPA-Rho-mDia signaling pathway that induces the capture and stabilization of microtubules in migrating fibroblasts was examined (4, 5). It was found that EB1 functioned downstream of LPA, Rho and mDia to stimulate stable microtubule formation. Dominant-negative EB1-C or knockdown of EB1 prevented stable microtubule formation in response to LPA stimulation. The function of EB1 in microtubule stabilization probably requires interaction with APC, as non-binding mutants of dominant-negative EB1-C and full-length EB1 were unable to inhibit or stimulate stable microtubule formation, respectively. Both EB1 and APC interacted with mDia directly, through domains that were distinct from those that interact with each other (FIG. 6f). EB1 and mDia1 coimmunoprecipitated with APC, but additional studies will be necessary to test whether all three proteins can enter into a single complex. Complex formation may be regulated by Rho activation of mDia, similarly to Cdc42/Rac activation of IQGAP and CLIP-170 (39). Binding of active Rho relieves the autoinhibition of mDia, a process thought to expose the FH1 and FH2 domains (36, 40, 41) that EB1 and APC bind to.

The formation of such a complex may contribute to microtubule stabilization either directly by capping microtubule plus ends, or indirectly by contributing to other (unidentified) factors that may cap the plus ends. The localization of these proteins at Glu-MT ends, and their proximity to the cortex as detected by TIRF microscopy, is consistent with such a complex stabilizing microtubule plus ends at cortical sites. However, these proteins were not detected on the ends of all Glu-MTs. This may reflect a more transient interaction of these proteins on stable microtubule ends, the difficulty of preserving these proteins on microtubule ends, or simply the technical difficulty of detecting small amounts of these proteins. Interestingly, a recent study has shown that mDia3 localizes to the kinetochore, a site consistent with mDia functioning on microtubule plus ends (42).

That EB1 and APC function along with the formin mDia to capture and stabilize microtubules strengthens the argument that the pathways regulating microtubule capture and stabilization in mammalian cells and budding yeast are evolutionarily conserved (FIG. 1a) (31). In both cases, a Rho-GTPase-regulated formin participates along with EB1. These results suggest that APC and Kar9, which bind EB1 and Bim1, respectively, may be functional homologues for microtubule capture and stabilization. In yeast, there is no evidence to date that Bim1 and Kar9 interact with Bni1; however, this has not been fully explored. Instead, it is thought that Bni1 contributes indirectly to microtubule capture by nucleating actin cable formation. Myo2 and kinesin motors participate in yeast microtubule capture (20, 21), but their function in mammalian microtubule stabilization has not yet been examined. This evolutionary conserved pathway results in captured microtubules with different fates: in yeast, microtubules are only transiently stabilized at bud sites, whereas in mammalian fibroblasts the microtubules exhibit long-term stabilization.

The mutant EB1 constructs show that EB1 must interact with other proteins to stabilize microtubules. This data points to APC as the most probable target. Besides APC (24), mammalian EB1 interacts with p150$^{Glued}$ (29, 30, 32) and the telomere-binding protein Pin2 (43). The effectiveness of EB1-C mutant constructs in blocking Glu-MT formation correlated with their binding to APC, but not to p150$^{Glued}$, suggesting that APC, but not p150$^{Glued}$, is involved in microtubule stabilization. This interpretation is consistent with previous results showing that the inhibition of dynactin, a complex containing p150$^{Glued}$, affects MTOC reorientation but not microtubule stabilization in fibroblasts (37). Also, a role for EB1 in MTOC reorientation was not observed, and overexpression of p150$^{Glued}$ did not stimulate stable microtubule formation. Thus, the interaction of EB1 and p150$^{Glued}$ (29, 30, 32) does not seem to be important for plus-end microtubule stabilization or MTOC reorientation. EB1 inhibits the microtubule polymerization activity of Pin2 (43), but the function of this interaction is unclear. Pin2 is expressed primarily in G2/M phase and localizes to spindle but not interphase microtubules (43), therefore the EB1-Pin2 interaction is unlikely to be important for stabilizing microtubules in migrating cells.

APC may not be the only EB1-binding protein involved in microtubule stabilization. Recently, EB1 was shown to interact with the Drosophila protein shortstop (44), although the binding site on EB1 was not identified. MACF/ACF7, the mammalian shortstop counterpart, has been shown to interact with microtubules (45-47) and function in microtubule stabilization (47, 48). MACF/ACF7 may function downstream of mDia as MACF/ACF7-knockout cells do not form stable microtubules in response to active mDia (48).

Members of the formin family of proteins have been shown to nucleate unbranched actin filaments (41, 49), and this activity has been proposed to be the principle mechanism by which formins regulate cellular processes. These results are the first to indicate that formin family members may regulate microtubules directly. Interestingly, the same region containing the FH1 and FH2 domains that is active in actin polymerization is also involved in APC and EB1 binding and microtubule stabilization. The binding of APC and/or EB1 may also affect the actin nucleating activity of mDia.

REFERENCES

1. Gundersen, G. G. & Bulinski, J. C. Microtubule arrays in differentiated cells contain elevated levels of a post-translationally modified form of tubulin. Eur. J. Cell Biol. 42, 288-294 (1986).
2. Gundersen, G. G. & Bulinski, J. C. Selective stabilization of microtubules oriented toward the direction of cell migration. Proc. Natl Acad. Sci. USA 85, 5946-5950 (1988).
3. Gundersen, G. G., Khawaja, S. & Bulinski, J. C. Generation of a stable, posttranslationally modified microtubule array is an early event in myogenic differentiation. J. Cell. Biol. 109, 2275-2288 (1989).
4. Cook, T. A., Nagasaki, T. & Gundersen, G. G. Rho guanosine triphosphatase mediates the selective stabilization of microtubules induced by lysophosphatidic acid. J. Cell Biol. 141, 175-185 (1998).
5. Palazzo, A. F., Cook, T. A., Alberts, A. S. & Gundersen, G. G. mDia mediates Rho-regulated formation and orientation of stable microtubules. Nature Cell Biol. 3, 723-729 (2001).
6. Palazzo, A. F., Eng, C. H., Schlaepfer, D. D., Marcantonio, E. E. & Gundersen, G. G. Localized stabilization of microtubules by integrin and FAK facilitated Rho signaling. Science 303, 836-839 (2004).
7. Webster, D. R., Gundersen, G. G., Bulinski, J. C. & Borisy, G. G. Differential turnover of tyrosinated and detyrosinated microtubules. Proc. Natl Acad. Sci. USA 84, 9040-9044 (1987).
8. Infante, A. S., Stein, M. S., Zhai, Y., Borisy, G. G. & Gundersen, G. G. Detyrosinated (Glu) microtubules are stabilized by an ATP-sensitive plus-end cap. J. Cell Sci. 113, 3907-3919 (2000).
9. Westermann, S. & Weber, K. Post-translational modifications regulate microtubule function. Nature Rev. Mol. Cell Biol. 4, 938-947 (2003).
10. Gundersen, G. G., Kalnoski, M. H. & Bulinski, J. C. Distinct populations of microtubules: tyrosinated and non-tyrosinated a-tubulin are distributed differently in vivo. Cell 38, 779-789 (1984).
11. Liao, G. & Gundersen, G. G. Kinesin is a candidate for cross-bridging microtubules and intermediate filaments. Selective binding of kinesin to detyrosinated tubulin and vimentin. J. Biol. Chem. 273, 9797-9803 (1998).
12. Lin, S. X., Gundersen, G. G. & Maxfield, F. R. Export from pericentriolar endocytic recycling compartment to cell surface depends on stable, detyrosinated (glu) microtubules and kinesin. Mol. Biol. Cell 13, 96-109 (2002).
13. Gurland, G. & Gundersen, G. G. Stable, detyrosinated microtubules function to localize vimentin intermediate filaments in fibroblasts. J. Cell Biol. 131, 1275-1290 (1995).
14. Kreitzer, G., Liao, G. & Gundersen, G. G. Detyrosination of tubulin regulates the interaction of intermediate filaments with microtubules in vivo via a kinesin-dependent mechanism. Mol. Biol. Cell 10, 1105-1118 (1999).
15. Schuyler, S. C. & Pellman, D. Microtubule "plus-end-tracking proteins": The end is just the beginning. Cell 105, 421-424 (2001).
16. Kohno, H., Tanaka, K., Mino, A., Umikawa, M. & Takai, Y. Bni1 implicated in cytoskeletal control is a putative target of Rholp small GTP binding protein in S. cerevisiae. EMBO J. 15, 6060-6068 (1996).
17. Lee, L., Klee, S. K., Evangelista, M., Boone, C. & Pellman, D. Control of mitotic spindle position by the Saccharomyces cerevisiae Formin Bni1p. J. Cell Biol. 144, 947-961 (1999).
18. Adames, N. R. & Cooper, J. A. Microtubule interactions with the cell cortex causing nuclear movements in Saccharomyces cerevisiae. J. Cell Biol. 149, 863-874 (2000).
19. Bloom, K. It's a kar9ochore to capture microtubules. Nature Cell Biol. 2, E96-E98 (2000).

20. Schuyler, S. C. & Pellman, D. Search, capture and signal: games microtubules and centrosomes play. J. Cell Sci. 114, 247-255 (2001).
21. Kusch, J., Liakopoulos, D. & Barral, Y. Spindle asymmetry: a compass for the cell. Trends Cell Biol. 13, 562-569 (2003).
22. Yin, H., Pruyne, D., Huffaker, T. C. & Bretscher, A. Myosin V orientates the mitotic spindle in yeast. Nature 406, 1013-1015 (2000).
23. Beach, D. L., Thibodeaux, J., Maddox, P., Yeh, E. & Bloom, K. The role of the proteins Kar9 and Myo2 in orienting the mitotic spindle of budding yeast. Curr. Biol. 10, 1497-1506 (2000).
24. Su, L. K. et al. APC binds to the novel protein EB1. Cancer Res. 55, 2971-2977 (1995).
25. Bienz, M. Spindles cotton on to junctions, APC and EB1. Nature Cell Biol. 3, E67-E68 (2001).
26. Munemitsu, S. et al. The APC gene product associates with microtubules in vivo and promotes their assembly in vitro. Cancer Res. 54, 3676-3681 (1994).
27. Berrueta, L. et al. The adenomatous polyposis coli-binding protein EB1 is associated with cytoplasmic and spindle microtubules. Proc. Natl Acad. Sci. USA 95, 10596-10601 (1998).
28. Zumbrunn, J., Kinoshita, K., Hyman, A. A. & Nathke, I. S. Binding of the adenomatous polyposis coli protein to microtubules increases microtubule stability and is regulated by GSK3β phosphorylation. Curr. Biol. 11, 44-49 (2001).
29. Askham, J. M., Vaughan, K. T., Goodson, H. V. & Morrison, E. E. Evidence that an interaction between EB1 and p150 (Glued) is required for the formation and maintenance of a radial microtubule array anchored at the centrosome. Mol. Biol. Cell 13, 3627-3645 (2002).
30. Ligon, L. A., Shelly, S. S., Tokito, M. & Holzbaur, E. L. The microtubule plus-end proteins EB1 and dynactin have differential effects on microtubule polymerization. Mol. Biol. Cell 14, 1405-1417 (2003).
31. Gundersen, G. G. Evolutionary conservation of microtubule-capture mechanisms. Nature Rev. Mol. Cell Biol. 3, 296-304 (2002).
32. Berrueta, L., Tirnauer, J. S., Schuyler, S. C., Pellman, D. & Bierer, B. E. The APC-associated protein EB1 associates with components of the dynactin complex and cytoplasmic dynein intermediate chain. Curr. Biol. 9, 425-428 (1999).
33. Tirnauer, J. S., O'Toole, E., Berrueta, L., Bierer, B. E. & Pellman, D. Yeast Bim1p promotes the G1-specific dynamics of microtubules. J. Cell Biol. 145, 993-1007 (1999).
34. Rogers, S. L., Rogers, G. C., Sharp, D. J. & Vale, R. D. Drosophila EB1 is important for proper assembly, dynamics, and positioning of the mitotic spindle. J. Cell Biol. 158, 873-884 (2002).
35. Mimori-Kiyosue, Y., Shiina, N. & Tsukita, S. The dynamic behavior of the APC-binding protein EB1 on the distal ends of microtubules. Curr. Biol. 10, 865-868 (2000).
36. Alberts, A. S. Identification of a carboxyl-terminal diaphanous-related formin homology protein autoregulatory domain. J. Biol. Chem. 276, 2824-2830 (2001).
37. Palazzo, A. F. et al. Cdc42, dynein, and dynactin regulate MTOC reorientation independent of Rho-regulated microtubule stabilization. Curr. Biol. 11, 1536-1541 (2001).
38. Askham, J. M., Moncur, P., Markham, A. F. & Morrison, E. E. Regulation and function of the interaction between the APC tumour suppressor protein and EB1. Oncogene 19, 1950-1958 (2000).
39. Fukata, M. et al. Rac1 and Cdc42 capture microtubules through IQGAP1 and CLIP-170. Cell 109, 873-885 (2002).
40. Watanabe, N., Kato, T., Fujita, A., Ishizaki, T. & Narumiya, S. Cooperation between mDia1 and ROCK in Rho-induced actin reorganization. Nature Cell Biol. 1, 136-143 (1999).
41. Wallar, B. J. & Alberts, A. S. The formins: active scaffolds that remodel the cytoskeleton. Trends Cell Biol. 13, 435-446 (2003).
42. Yasuda, S. et al. Cdc42 and mDia3 regulate microtubule attachment to kinetochores. Nature 428, 767-771 (2004).
43. Nakamura, M., Zhou, X. Z., Kishi, S. & Lu, K. P. Involvement of the telomeric protein Pin2/TRF1 in the regulation of the mitotic spindle. FEBS Lett. 514, 193-198 (2002).
44. Subramanian, A. et al. Shortstop recruits EB1/APC1 and promotes microtubule assembly at the muscle-tendon junction. Curr. Biol. 13, 1086-1095 (2003).
45. Leung, C. L., Sun, D., Zheng, M., Knowles, D. R. & Liem, R. K. Microtubule actin cross-linking factor (MACF): a hybrid of dystonin and dystrophin that can interact with the actin and microtubule cytoskeletons. J. Cell Biol. 147, 1275-1286 (1999).
46. Karakesisoglou, I., Yang, Y. & Fuchs, E. An epidermal plakin that integrates actin and microtubule networks at cellular junctions. J. Cell Biol. 149, 195-208 (2000).
47. Sun, D., Leung, C. L. & Liem, R. K. Characterization of the microtubule binding domain of microtubule actin crosslinking factor (MACF) : identification of a novel group of microtubule associated proteins. J. Cell Sci. 114, 161-172 (2001).
48. Kodama, A., Karakesisoglou, I., Wong, E., Vaezi, A. & Fuchs, E. ACF7. An essential integrator of microtubule dynamics. Cell 115, 343-354 (2003).
49. Evangelista, M., Zigmond, S. & Boone, C. Formins: signaling effectors for assembly and polarization of actin filaments. J. Cell Sci. 116, 2903-2911 (2003).
50. Elbashir, S. M., Harborth, J., Weber, K. & Tuschl, T. Analysis of gene function in somatic mammalian cells using small interfering RNAs. Methods 26, 199-213 (2002).

What is claimed is:

1. A nucleic acid which, when introduced in vivo into a mammalian cell endogenously expressing an EB1 polypeptide encoded by the nucleotide sequence set forth in SEQ ID NO:1, inhibits the expression of EB1 in such mammalian cell by greater than 80%, thereby reducing the amount of stable microtubules in the mammalian cell, wherein the nucleic acid is an siRNA comprising SEQ. ID. NO.:7.

2. A composition comprising (a) a nucleic acid which, when introduced in vivo into a mammalian cell endogenously expressing an EB1 polypeptide encoded by the nucleotide sequence set forth in SEQ ID NO:1, inhibits the expression of EB1 in such mammalian cell by greater than 80%, thereby reducing the amount of stable microtubules in the cell, and (b) a pharmaceutically acceptable carrier, wherein the nucleic acid is an siRNA comprising SEQ. ID. NO.:7.

3. A vector which comprises the nucleic acid of claim 1.

4. The vector of claim 3, wherein the vector is an expression vector.

5. A composition comprising (a) a vector encoding a nucleic acid which, when introduced in vivo into a mammalian cell endogenously expressing an EB1 polypeptide encoded by the nucleotide sequence set forth in SEQ ID NO:1, inhibits the expression of EB1 in such mammalian cell by greater than 80%, thereby reducing the amount of stable microtubules in the cell, and (b) a pharmaceutically acceptable carrier, wherein the nucleic acid is an siRNA comprising SEQ. ID. NO.:7.

* * * * *

SEQUENCE LISTING

<160> NUMBER OF SEQ ID NOS: 7

<210> SEQ ID NO 1
<211> LENGTH: 807
<212> TYPE: DNA
<213> ORGANISM: Homo sapiens

<400> SEQUENCE: 1

```
atggcagtga acgtatactc aacgtcagtg accagtgata acctaagtcg acatgacatg    60
ctggcctgga tcaatgagtc tctgcagttg aatctgacaa agatcgaaca gttgtgctca   120
ggggctgcgt attgtcagtt tatggacatg ctgttccctg gctccattgc cttgaagaaa   180
gtgaaattcc aagctaagct agaacacgag tacatccaga acttcaaaat actacaagca   240
ggttttaaga gaatgggtgt tgacaaaata attcctgtgg acaaattagt aaaaggaaag   300
tttcaggaca attttgaatt cgttcagtgg ttcaagaagt ttttcgatgc aaactatgat   360
ggaaaagact atgaccctgt ggctgccaga caaggtcaag aaactgcagt ggctccttcc   420
cttgttgctc cagctctgaa taaaccgaag aaacctctca cttctagcag tgcagctccc   480
cagaggccca tctcaacaca gagaaccgct gcggctccta aggctggccc tggtgtggtg   540
cgaaagaacc tggtgtgggc aacggagac gacgaggcag ctgagttgat gcagcaggtc    600
aacgtattga aacttactgt tgaagacttg agaaagaga gggatttcta cttcggaaag   660
ctacggaaca ttgaattgat ttgccaggag aacgaggggg aaaacgaccc tgtattgcag   720
aggattgtag acattctgta tgccacagat gaaggctttg tgatacctga tgaagggggc   780
ccacaggagg agcaagaaga gtattaa                                       807
```

<210> SEQ ID NO 2
<211> LENGTH: 268
<212> TYPE: PRT
<213> ORGANISM: Homo sapiens

<400> SEQUENCE: 2

```
Met Ala Val Asn Val Tyr Ser Thr Ser Val Thr Ser Asp Asn Leu Ser
1               5                   10                  15

Arg His Asp Met Leu Ala Trp Ile Asn Glu Ser Leu Gln Leu Asn Leu
                20                  25                  30

Thr Lys Ile Glu Gln Leu Cys Ser Gly Ala Ala Tyr Cys Gln Phe Met
            35                  40                  45

Asp Met Leu Phe Pro Gly Ser Ile Ala Leu Lys Lys Val Lys Phe Gln
    50                  55                  60

Ala Lys Leu Glu His Glu Tyr Ile Gln Asn Phe Lys Ile Leu Gln Ala
65                  70                  75                  80

Gly Phe Lys Arg Met Gly Val Asp Lys Ile Ile Pro Val Asp Lys Leu
                85                  90                  95

Val Lys Gly Lys Phe Gln Asp Asn Phe Glu Phe Val Gln Trp Phe Lys
            100                 105                 110

Lys Phe Phe Asp Ala Asn Tyr Asp Gly Lys Asp Tyr Asp Pro Val Ala
        115                 120                 125

Ala Arg Gln Gly Gln Glu Thr Ala Val Ala Pro Ser Leu Val Ala Pro
    130                 135                 140

Ala Leu Asn Lys Pro Lys Lys Pro Leu Thr Ser Ser Ser Ala Ala Pro
145                 150                 155                 160

Gln Arg Pro Ile Ser Thr Gln Arg Thr Ala Ala Ala Pro Lys Ala Gly
                165                 170                 175

Pro Gly Val Val Arg Lys Asn Pro Gly Val Gly Asn Gly Asp Asp Glu
            180                 185                 190

Ala Ala Glu Leu Met Gln Gln Val Asn Val Leu Lys Leu Thr Val Glu
        195                 200                 205

Asp Leu Glu Lys Glu Arg Asp Phe Tyr Phe Gly Lys Leu Arg Asn Ile
    210                 215                 220
```

```
Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Gln Glu Glu Tyr
            260                 265

<210> SEQ ID NO 3
<211> LENGTH: 2578
<212> TYPE: DNA
<213> ORGANISM: Homo sapiens

<400> SEQUENCE: 3
```

| | | | | | |
|---|---|---|---|---|---|
| cgagcaggcg | gcaggcacgg | tccgtgcgga | gaggcgagcg | agcgggaaga | cgcagccacc | 60 |
| ttcctcacca | gccagcccac | agcggtttgt | tccccttctc | gggagtgcgc | caatgcctgg | 120 |
| gccgacccaa | accctgtccc | caaatggcga | gaacaacaac | gacatcatcc | aggataataa | 180 |
| cgggaccatc | attcctttcc | ggaagcacac | agtgcgcggg | gagcgttcct | acagttgggg | 240 |
| aatggcggtc | aatgtgtatt | ctacctcgat | aacccaagag | actatgagca | gacatgacat | 300 |
| cattgcatgg | gttaatgaca | tagtatcttt | aaactacaca | aaagtggaac | agctttgttc | 360 |
| aggagcggcc | tattgccaat | tcatggacat | gctcttccct | ggctgcatta | gtttgaagaa | 420 |
| agtaaaattt | caagcaaagc | tggaacatga | atatattcac | aattttaaac | ttctgcaagc | 480 |
| atcatttaag | cgaatgaacg | ttgataaggt | aattccagtg | gagaagctag | tgaaaggacg | 540 |
| tttccaggac | aacctggatt | ttattcaatg | gtttaagaaa | ttctatgatg | ctaactacga | 600 |
| tgggaaggag | tatgatcctg | tagaggcacg | acaagggcaa | gatgcaattc | ctcctcctga | 660 |
| ccctggtgaa | cagatcttca | acctgccaaa | aaagtctcac | catgcaaact | cccccacagc | 720 |
| aggtgcagct | aaatcaagtc | cagcagctaa | accaggatcc | acaccttctc | gaccctcatc | 780 |
| agccaaaagg | gcttcttcca | gtggctcagc | atccaaatcc | gataaagatt | tagaaacgca | 840 |
| ggtcatacag | cttaatgaac | aggtacattc | attaaaactt | gcccttgaag | gcgtggaaaa | 900 |
| ggaaagggat | ttctactttg | ggaagttgag | agagatcgag | ctactctgcc | aagaacacgg | 960 |
| gcaggaaaat | gatgacctcg | tgcagagact | aatggacatc | ctgtatgctt | cagaagaaca | 1020 |
| cgagggccac | acagaagagc | cggaagcaga | ggagcaagcc | cacgaacagc | agcccccgca | 1080 |
| gcaggaagag | tactgaccca | ccccggctgc | tcttgacact | tccattgtgt | gtgggaacgt | 1140 |
| ttcttctgga | gaattggaac | atgtgtggcc | ccaagctcaa | cagaaccag | ttgttcccaa | 1200 |
| tctgccgtta | ccatcaacgc | actgttgcat | atgccagcca | ctgcgcttgg | ttcccatttt | 1260 |
| ctttgctaag | gtgtattagc | ggacggccct | ctggccacct | acccgagaga | tcgtagggtc | 1320 |
| acattcatcc | aacttcacca | cttggctgct | tgagattggt | tctgctcttt | tcttcattcc | 1380 |
| tttccagaac | aactctttcc | caccccaaca | ccactgccac | cacccctctt | tttatcctgg | 1440 |
| tgtgaaacaa | tggtaatttg | atatatggta | tttatattgg | catttttcaa | cccagtgtca | 1500 |
| ctagatgtca | cacacatttg | tggtgctttg | atgtttgcaa | gtctaacctc | tgaacataaa | 1560 |
| tttggtcaaa | taattggaac | aaagggaaac | agatacttga | tatgaaagcc | ataatgacgg | 1620 |
| tgacttgtgt | cgtgggggaa | aacataaggt | cattttctcc | ctctactcac | aatactaaag | 1680 |
| ggaaaaaatg | gattcaaagc | taggatttca | gggcccagca | gtgttcctcc | atcagcatgt | 1740 |
| tagacaacta | cacagtatgt | tgttagtttt | gaaagacatt | cactcaagga | aaacaccatc | 1800 |
| tcaactttgc | ccgctcacca | tgtcccttgc | ccccatgtag | cccatttccc | aggttatgct | 1860 |

-continued

```
cttttctttc tcagggtcct ctttggtggg cagccactcc ccgagatgtt gccatcagtt    1920
ttctgcagtc caaagagggt atggttaggt acgggtcttc ctgcctcatt cctcttcctc    1980
tttgtgtagg tttcagccac aaaactgtca ttcactctag ggacccctta ctaaagggta    2040
acttcaggtg tgcagccctg agctccaagg ctctgcacca tgccacacac ttgctgtaag    2100
gctagaagtg aagaccttat aataggagc ataattgcga gggagaatca tggttctgca    2160
gtctggtgta gacactggaa taacagcaca gaaaaatcta tgactcccaa tatcttctag    2220
aataaagaat tttccctctt taacacaagg gccctccttg tcattgacct tagctaaacc    2280
atggcaattc ataaatagag gaaacattaa tgaattaaaa gcattcctta ttttttaact    2340
aatatttgta cattttctta gtctctttcc aagtctttgc ctctttttt tctttatttt     2400 tatttttttcc tttgacagat ggtatccctt cctggatcat tcatttcacc ttggtttcta   2460
actttaggtt tacttttcact tgttatttga cttagcaggt gcaacaaaaa caagaaacaa    2520
atgtgcccac cccactttcc gcttaactga aaagcttaaa ataaatttcc gaattatg      2578
```

<210> SEQ ID NO 4
<211> LENGTH: 327
<212> TYPE: PRT
<213> ORGANISM: Homo sapiens

<400> SEQUENCE: 4

```
Met Pro Gly Pro Thr Gln Thr Leu Ser Pro Asn Gly Glu Asn Asn Asn
1               5                   10                  15

Asp Ile Ile Gln Asp Asn Asn Gly Thr Ile Ile Pro Phe Arg Lys His
            20                  25                  30

Thr Val Arg Gly Glu Arg Ser Tyr Ser Trp Gly Met Ala Val Asn Val
        35                  40                  45

Tyr Ser Thr Ser Ile Thr Gln Glu Thr Met Ser Arg His Asp Ile Ile
    50                  55                  60

Ala Trp Val Asn Asp Ile Val Ser Leu Asn Tyr Thr Lys Val Glu Gln
65                  70                  75                  80

Leu Cys Ser Gly Ala Ala Tyr Cys Gln Phe Met Asp Met Leu Phe Pro
                85                  90                  95

Gly Cys Ile Ser Leu Lys Lys Val Lys Phe Gln Ala Lys Leu Glu His
            100                 105                 110

Glu Tyr Ile His Asn Phe Lys Leu Leu Gln Ala Ser Phe Lys Arg Met
        115                 120                 125

Asn Val Asp Lys Val Ile Pro Val Glu Lys Leu Val Lys Gly Arg Phe
    130                 135                 140

Gln Asp Asn Leu Asp Phe Ile Gln Trp Phe Lys Lys Phe Tyr Asp Ala
145                 150                 155                 160

Asn Tyr Asp Gly Lys Glu Tyr Asp Pro Val Glu Ala Arg Gln Gly Gln
                165                 170                 175

Asp Ala Ile Pro Pro Asp Pro Gly Glu Gln Ile Phe Asn Leu Pro
            180                 185                 190

Lys Lys Ser His His Ala Asn Ser Pro Thr Ala Gly Ala Ala Lys Ser
        195                 200                 205

Ser Pro Ala Ala Lys Pro Gly Ser Thr Pro Ser Arg Pro Ser Ser Ala
    210                 215                 220

Lys Arg Ala Ser Ser Ser Gly Ser Ala Ser Lys Ser Asp Lys Asp Leu
225                 230                 235                 240
```

```
Glu Thr Gln Val Ile Gln Leu Asn Glu Gln Val His Ser Leu Lys Leu
            245                 250                 255

Ala Leu Glu Gly Val Glu Lys Glu Arg Asp Phe Tyr Phe Gly Lys Leu
        260                 265                 270

Arg Glu Ile Glu Leu Leu Cys Gln Glu His Gly Gln Glu Asn Asp Asp
        275                 280                 285

Leu Val Gln Arg Leu Met Asp Ile Leu Tyr Ala Ser Glu Glu His Glu
        290                 295                 300

Gly His Thr Glu Glu Pro Glu Ala Glu Glu Gln Ala His Glu Gln Gln
305                 310                 315                 320

Pro Pro Gln Gln Glu Glu Tyr
            325

<210> SEQ ID NO 5
<211> LENGTH: 1880
<212> TYPE: DNA
<213> ORGANISM: Homo sapiens

<400> SEQUENCE: 5
tctctgtgcg ttgaagccgg agaccgcggc ggcctcagcg aggaccctcc gccccggagc    60
cgccggccgg agccgcagcc tctgccgcag cgccccgcc acctgtcccc tcccctccg    120 cctccgccgg agccgcctcg tgcactctgg ggtatggccg tcaatgtgta ctccacatct    180
gtgaccagtg aaaatctgag tcgccatgat atgcttgcat gggtcaacga ctccctgcac    240
ctcaactata ccaagataga acagcttttgt tcagggcag cctactgcca gttcatggac    300
atgctcttcc ccggctgtgt gcacttgagg aaagtgaagt tccaggccaa actagagcat    360
gaatacatcc acaacttcaa ggtgctgcaa gcagctttca agaagatggg tgttgacaaa    420
atcattcctg tagagaaatt agtgaaagga aaattccaag ataattttga gtttattcag    480
tggtttaaga aattctttga cgcaaactat gatggaaagg attacaaccc tctgctggcg    540
cggcagggcc aggacgtagc gccacctcct aacccaggtg atcagatctt caacaaatcc    600
aagaaactca ttggcacagc agttccacag gaggacgtcc ccacaggccc aaaaaacatg    660
cagacctctg gccggctgag caatgtggcc cccccctgca ttctccggaa gaatcctcca    720
tcagcccgaa atggcggcca tgagactgat gcccaaattc ttgaactcaa ccaacagctg    780
gtggacttga agctgacagt ggatgggctg agaaggaac gtgacttcta cttcagcaaa    840
cttcgtgaca tcgagctcat ctgccaggag catgaaagtg aaaacagccc tgttatctca    900
ggcatcattg gcatcctcta tgccacagag gaaggattcg caccccctga ggacgatgag    960
attgaagagc atcaacaaga agaccaggac gagtactgag ggcggccgca gccctggctg   1020
actgcacggc ttccccgtgc ctccctccct gctccactcc acattatag tccttttccta   1080 acacggtcgg ccgggtgctt tgtgtcagtg ctgcagcact ggggagccag gcgagggggg   1140 cttggggca tggggccgga aagcaggcag aagcccgtcc tgggtggtgc tggcccagtt   1200
ggtgggaccc ctgtccacac ccaccctatt tatttccgtt gtctctctgc tgtgtcgccc   1260
aacacttccc agggtgctgc tgccaccccgc cccagccagc cacctgctcc tgacagccag   1320
cagctgtgta tttgacaaag tcattggtat atttttactt actggattct ccttgcactt   1380
tacctgttct tttccagagc tgacagcacg ggctccggcg cagtgtgcct ggcttggctt   1440 cccttccccca tggctggggg ctggggtagg actcacccat tctaatttat tttgtctttt   1500
ggcttctcag tagctaaggg gaaggctgat gtcaggagag ggagaggggg ctgaggaggt   1560
agtgctgtag gcccaggggg tcagggaaag ggagggggc atgtgaggga tggaaatgac   1620
```

-continued

```
ctcctggcac caggctcacc cacccaaggc ccctgcccc agcactgaat cccagcgctg    1680
ccctgaggcc cccagccact ccctccagca gcctggttca ccacacaaac tctgcctgga   1740
ccccattgtc tgtctgcttc ccacctgccc tccccacccc ctgcccctcg ggcaccagcc   1800
tgcatatgtg ttcacttta tttaaataaa cttgtgtggt aaaagtacat gccatgtgtc    1860
cctcaactga aaaaaaaaa                                                 1880
```

<210> SEQ ID NO 6
<211> LENGTH: 281
<212> TYPE: PRT
<213> ORGANISM: Homo sapiens

<400> SEQUENCE: 6

```
Met Ala Val Asn Val Tyr Ser Thr Ser Val Thr Ser Glu Asn Leu Ser
1               5                   10                  15

Arg His Asp Met Leu Ala Trp Val Asn Asp Ser Leu His Leu Asn Tyr
            20                  25                  30

Thr Lys Ile Glu Gln Leu Cys Ser Gly Ala Ala Tyr Cys Gln Phe Met
        35                  40                  45

Asp Met Leu Phe Pro Gly Cys Val His Leu Arg Lys Val Lys Phe Gln
    50                  55                  60

Ala Lys Leu Glu His Glu Tyr Ile His Asn Phe Lys Val Leu Gln Ala
65                  70                  75                  80

Ala Phe Lys Lys Met Gly Val Asp Lys Ile Ile Pro Val Glu Lys Leu
                85                  90                  95

Val Lys Gly Lys Phe Gln Asp Asn Phe Glu Phe Ile Gln Trp Phe Lys
            100                 105                 110

Lys Phe Phe Asp Ala Asn Tyr Asp Gly Lys Asp Tyr Asn Pro Leu Leu
        115                 120                 125

Ala Arg Gln Gly Gln Asp Val Ala Pro Pro Asn Pro Gly Asp Gln
    130                 135                 140

Ile Phe Asn Lys Ser Lys Lys Leu Ile Gly Thr Ala Val Pro Gln Arg
145                 150                 155                 160

Thr Ser Pro Thr Gly Pro Lys Asn Met Gln Thr Ser Gly Arg Leu Ser
                165                 170                 175

Asn Val Ala Pro Pro Cys Ile Leu Arg Lys Asn Pro Ser Ala Arg
            180                 185                 190

Asn Gly Gly His Glu Thr Asp Ala Gln Ile Leu Glu Leu Asn Gln Gln
        195                 200                 205

Leu Val Asp Leu Lys Leu Thr Val Asp Gly Leu Glu Lys Glu Arg Asp
    210                 215                 220

Phe Tyr Phe Ser Lys Leu Arg Asp Ile Glu Leu Ile Cys Gln Glu His
225                 230                 235                 240

Glu Ser Glu Asn Ser Pro Val Ile Ser Gly Ile Ile Gly Ile Leu Tyr
                245                 250                 255

Ala Thr Glu Glu Gly Phe Ala Pro Pro Glu Asp Asp Glu Ile Glu Glu
            260                 265                 270

His Gln Gln Glu Asp Gln Asp Glu Tyr
        275                 280
```

<210> SEQ ID NO 7
<211> LENGTH: 21
<212> TYPE: RNA
<213> ORGANISM: artificial
<220> FEATURE:

```
-continued

<223> OTHER INFORMATION: EB1 siRNA sequence; nucleotides 181-199

<400> SEQUENCE: 7
aagugaaauu ccaagcuaag c                                           21
```